United States Patent
Flower et al.

(10) Patent No.: US 11,883,598 B2
(45) Date of Patent: Jan. 30, 2024

(54) MASK AND MASK-MOUNTED FLOW GENERATOR SYSTEM

(71) Applicant: ResMed Pty Ltd, Bella Vista (AU)

(72) Inventors: Renee Frances Flower, Sydney (AU); Philip Rodney Kwok, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 570 days.

(21) Appl. No.: 16/998,434

(22) Filed: Aug. 20, 2020

(65) Prior Publication Data

US 2020/0376220 A1    Dec. 3, 2020

Related U.S. Application Data

(63) Continuation of application No. 15/952,988, filed on Apr. 13, 2018, now abandoned, which is a (Continued)

(30) Foreign Application Priority Data

Sep. 7, 2006 (AU) ................................ 2006904900
Oct. 27, 2006 (AU) ................................ 2006905967

(51) Int. Cl.
  *A61M 16/06* (2006.01)
  *A61M 16/00* (2006.01)
  *A61M 16/08* (2006.01)

(52) U.S. Cl.
  CPC ........ *A61M 16/06* (2013.01); *A61M 16/0066* (2013.01); *A61M 16/0069* (2014.02);
  (Continued)

(58) Field of Classification Search
  CPC .......... A61M 16/0003; A61M 16/0066; A61M 16/0069; A61M 16/06; A61M 16/0858;
  (Continued)

(56) References Cited

U.S. PATENT DOCUMENTS 3,629,868 A  12/1971  Greenlee
3,803,690 A   4/1974  Cann et al.
(Continued)

FOREIGN PATENT DOCUMENTS

DE    102 61 602 A1   7/2004
EP      0 066 451 A1  8/1985
(Continued)

OTHER PUBLICATIONS

Extended European Search Report dated Sep. 15, 2017 issued in European Application No. 07800279.7 (8 pages).
(Continued)

*Primary Examiner* — Kathryn E Ditmer
(74) *Attorney, Agent, or Firm* — Nixon & Vanderhye P.C.

(57) ABSTRACT

A system for delivering a pressurized flow of breathable gas to a patient includes a patient interface and a flow generator mounted on the patient interface. The patient interface is configured to contact the patient's head and includes a frame and a cushion supported by the frame and configured to sealingly connect the patient interface to the patient's face and form a chamber between the frame and the patient's face. An inlet port in the frame is configured to receive the pressurized flow of breathable gas. The flow generator is configured to generate the pressurized flow and is capable of creating a pressure of about 2-40 cm $H_2O$ in the chamber. In addition, a pressure sensor assembly spans from an outlet port of the flow generator to the inlet port of the patient interface.

16 Claims, 17 Drawing Sheets

Related U.S. Application Data continuation of application No. 12/438,899, filed as application No. PCT/AU2007/001325 on Sep. 6, 2007, now abandoned.

(52) U.S. Cl.
CPC ..... *A61M 16/0858* (2014.02); *A61M 16/0638* (2014.02); *A61M 16/0683* (2013.01); *A61M 2016/0027* (2013.01); *A61M 2016/0033* (2013.01); *A61M 2205/0238* (2013.01); *A61M 2205/3368* (2013.01); *A61M 2205/3569* (2013.01); *A61M 2205/3592* (2013.01); *A61M 2205/42* (2013.01); *A61M 2205/502* (2013.01); *A61M 2205/8206* (2013.01); *A61M 2209/088* (2013.01)

(58) Field of Classification Search
CPC .... A61M 2016/0027; A61M 2016/003; A61M 2016/0033
See application file for complete search history.

(56) References Cited

U.S. PATENT DOCUMENTS

| | | | |
|---|---|---|---|
| 3,989,037 | A | 11/1976 | Franetzki |
| 4,019,508 | A * | 4/1977 | Der Estephanian ......................... A61M 16/1065 128/202.19 |
| 4,083,245 | A | 4/1978 | Osborn |
| 4,190,131 | A | 2/1980 | Robinson |
| 4,220,161 | A | 9/1980 | Berlin |
| 4,233,972 | A | 11/1980 | Hauff et al. |
| 4,297,999 | A | 11/1981 | Kitrell |
| 4,440,177 | A | 4/1984 | Anderson |
| 4,590,951 | A | 5/1986 | O'Connor |
| 4,993,269 | A | 2/1991 | Guillaume |
| 5,137,026 | A | 8/1992 | Waterson |
| 5,245,995 | A | 9/1993 | Sullivan |
| 5,303,701 | A | 4/1994 | Heins et al. |
| 5,318,020 | A | 6/1994 | Schegerin |
| 5,332,188 | A | 7/1994 | Davis et al. |
| 5,357,972 | A | 10/1994 | Norlien |
| 5,372,130 | A | 12/1994 | Stern |
| 5,404,874 | A | 4/1995 | Meier |
| 5,711,033 | A | 1/1998 | Green |
| 5,970,801 | A | 10/1999 | Ciobanu |
| 5,996,580 | A | 12/1999 | Swann |
| 6,216,691 | B1 * | 4/2001 | Kenyon ................. F01C 21/10 128/205.18 |
| 6,435,184 | B1 | 8/2002 | Ho |
| 6,513,526 | B2 | 2/2003 | Kwok et al. |
| 6,561,190 | B1 | 5/2003 | Kwok |
| 6,561,191 | B1 | 5/2003 | Kwok |
| 6,772,760 | B2 | 8/2004 | Frater et al. |
| 6,772,762 | B2 | 8/2004 | Piesinger |
| 6,837,260 | B1 | 1/2005 | Kuehn |
| 6,895,962 | B2 | 5/2005 | Kullik et al. |
| 6,910,483 | B2 | 6/2005 | Daly et al. |
| 7,617,823 | B2 | 11/2009 | DiMatteo et al. |
| 7,913,692 | B2 | 3/2011 | Kwok |
| 7,975,688 | B1 | 7/2011 | Truitt |
| 8,006,691 | B2 | 8/2011 | Kenyon et al. |
| 8,997,742 | B2 | 4/2015 | Moore |
| 9,180,266 | B1 | 11/2015 | Sherman |
| 2002/0022973 | A1 | 2/2002 | Sun et al. |
| 2002/0029777 | A1 | 3/2002 | Zimprich et al. |
| 2003/0062045 | A1 | 4/2003 | Woodring et al. |
| 2003/0154980 | A1 * | 8/2003 | Berthon-Jones .... A61M 16/022 128/204.22 |
| 2003/0172930 | A1 | 9/2003 | Kullik |
| 2004/0016432 | A1 * | 1/2004 | Genger ............ A61M 16/0694 128/204.23 |
| 2004/0079373 | A1 | 4/2004 | Mukaiyama et al. |
| 2004/0210154 | A1 | 10/2004 | Kline |
| 2004/0249300 | A1 | 12/2004 | Miller |
| 2005/0034724 | A1 | 2/2005 | O'Dea |
| 2005/0061321 | A1 | 3/2005 | Jones |
| 2005/0103339 | A1 | 5/2005 | Daly et al. |
| 2006/0096596 | A1 | 5/2006 | Occhialini et al. |
| 2006/0117856 | A1 | 6/2006 | Orr |
| 2006/0150973 | A1 | 7/2006 | Chalvignac |
| 2006/0162729 | A1 | 7/2006 | Ging et al. |
| 2006/0213523 | A1 | 9/2006 | VanDerWoude |
| 2006/0237013 | A1 | 10/2006 | Kwok |
| 2006/0283460 | A1 | 12/2006 | Brown et al. |
| 2007/0000493 | A1 | 1/2007 | Cox |
| 2007/0048159 | A1 * | 3/2007 | DiMatteo .......... A61M 16/0066 417/423.14 |
| 2007/0251527 | A1 | 11/2007 | Sleeper |
| 2007/0277825 | A1 | 12/2007 | Bordewick et al. |
| 2007/0277827 | A1 | 12/2007 | Bordewick et al. |
| 2008/0060649 | A1 | 3/2008 | Veliss et al. |
| 2008/0092898 | A1 | 4/2008 | Schneider |
| 2008/0216831 | A1 | 9/2008 | McGinnis |
| 2008/0304986 | A1 | 12/2008 | Kenyon et al. |
| 2009/0007912 | A1 | 1/2009 | Lindell |
| 2009/0133697 | A1 * | 5/2009 | Kwok ................ A61M 16/0858 128/205.25 |
| 2009/0320842 | A1 | 12/2009 | Doherty et al. |
| 2012/0152255 | A1 | 6/2012 | Barlow et al. |
| 2012/0167879 | A1 | 7/2012 | Bowman et al. |
| 2018/0236197 | A1 | 8/2018 | Flower et al. |

FOREIGN PATENT DOCUMENTS

| | | |
|---|---|---|
| EP | 0 164 946 A2 | 12/1985 |
| EP | 0 558 147 A1 | 9/1993 |
| EP | 0 528 733 A1 | 9/1996 |
| EP | 1 318 307 A1 | 6/2003 |
| EP | 1 655 052 A2 | 5/2006 |
| GB | 2 209 474 A | 5/1989 |
| GB | 2 215 216 A | 9/1989 |
| WO | WO 99/13931 | 3/1999 |
| WO | 2004/112873 A1 | 12/2004 |
| WO | 2005/028009 A1 | 3/2005 |
| WO | WO 2005/028009 A1 | 3/2005 |
| WO | WO-2005028009 A1 * | 3/2005 ........ A61M 16/0057 |
| WO | WO 2005/063328 A1 | 7/2005 |
| WO | WO 2007/048205 A1 | 5/2007 |
| WO | WO 2007/048206 A1 | 5/2007 |
| WO | WO 2007/117716 A2 | 10/2007 |
| WO | WO 2007/124108 A2 | 11/2007 |
| WO | WO 2007/134405 A1 | 11/2007 |
| WO | WO 2008/028247 A1 | 3/2008 |
| WO | WO 2008/108789 A1 | 9/2008 |

OTHER PUBLICATIONS

International Search Report dated Oct. 23, 2007 in PCT/AU2007/001325.
N Tandon, "Noise-Reducing Designs of Machines and Structures," Sādhanā,, vol. 25, Part 3, Jun. 2000, pp. 331-339.
U.S. Appl. No. 60/494,119, filed Aug. 2003, Gunaratnam et al..
U.S. Appl. No. 29/274,504, filed Apr. 2007, Kenyon.
U.S. Appl. No. 29/274,505, filed Apr. 2007, Kenyon.
U.S. Appl. No. 29/274,506, filed Apr. 2007, Kenyon.

* cited by examiner

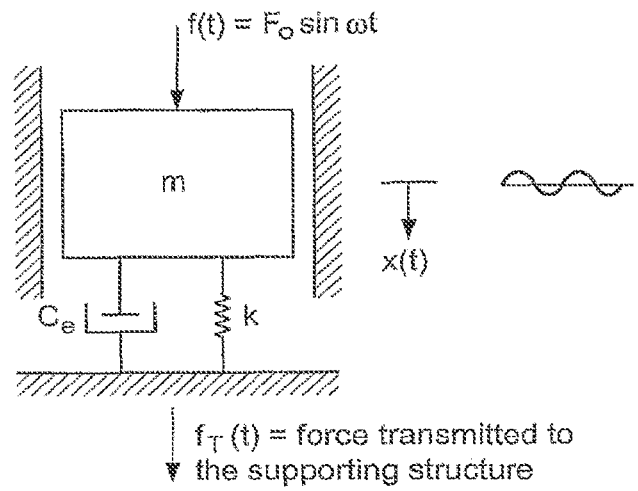
FIG. 15
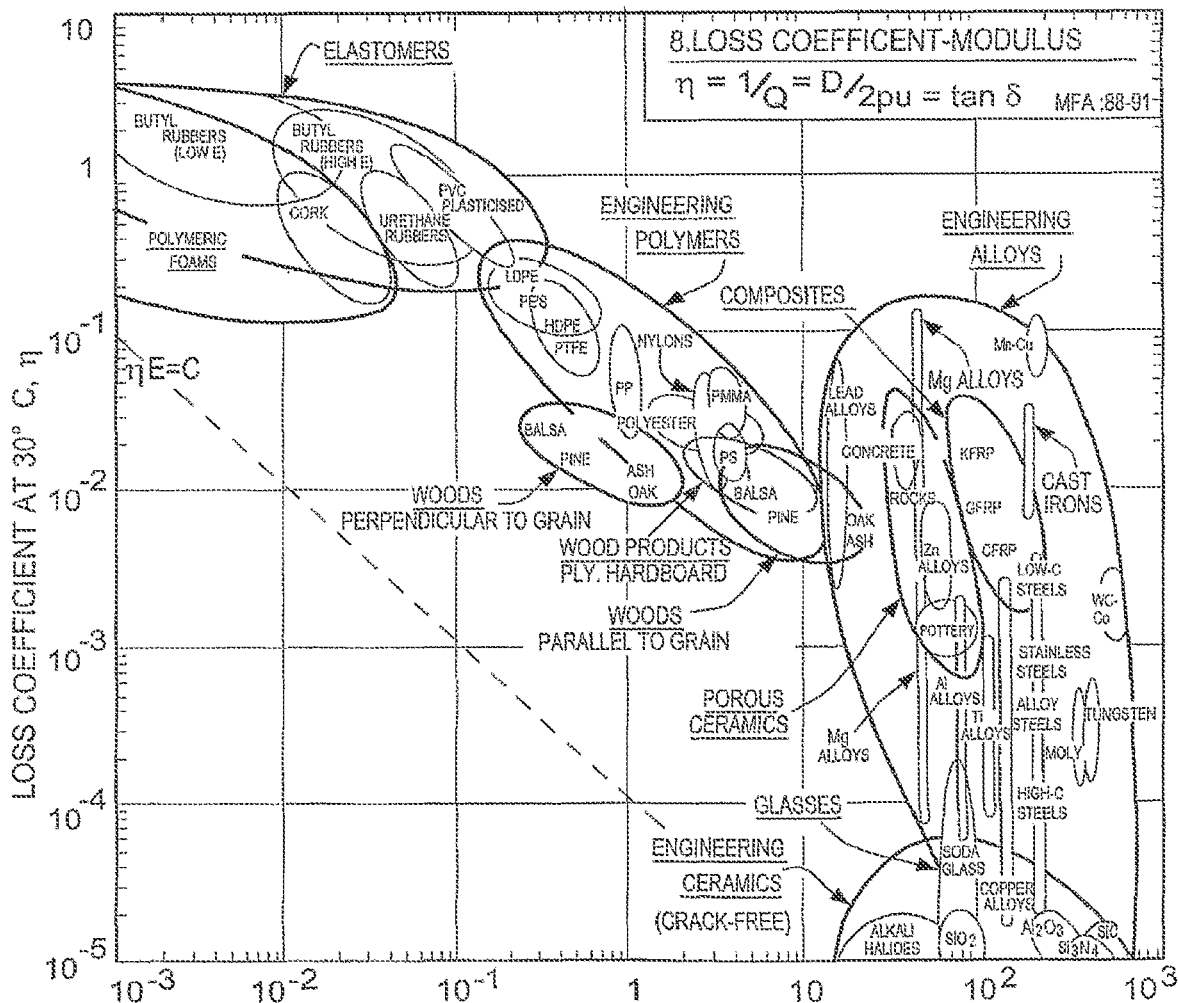
FIG. 16 YOUNG'S MODULUS, E (GPa)

MASK AND MASK-MOUNTED FLOW GENERATOR SYSTEM

CROSS-REFERENCE TO RELATED APPLICATIONS

This application is a continuation of U.S. application Ser. No. 15/952,988, filed Apr. 13, 2018, which is a continuation of U.S. application Ser. No. 12/438,899, filed Feb. 25, 2009, which is the U.S. national phase of International Application No. PCT/AUI2007/001325, filed Sep. 6, 2007, which designated the U.S. and claims priority to Australian Provisional Applications 2006904900 and 2006905967, filed Sep. 7, 2006 and Oct. 27, 2006, respectively, the entire contents of which are incorporated herein by reference. WO 2005/028009 is also incorporated herein by reference in its entirety.

BACKGROUND OF THE INVENTION

1. Field of the Invention

The present invention relates to respiratory therapies, including but not limited to, Continuous Positive Airway Pressure (CPAP), bi-level and ventilation therapies. The present invention also relates to a mask and flow generator system that delivers a flow of pressurized breathable gas, e.g. air, to a patient for treatment of various breathing disorders. Tue present invention further relates to a system in which the flow generator is incorporated with the mask or a headgear that supports the mask.

2. Description of the Related Art

Obstructive Sleep Apnea (OSA) is a sleep breathing disorder (SBD). For those who have OSA when they sleep the soft tissue in their throat and airway relax and collapse thus blocking the airway and preventing airflow to the lungs. This cessation of breathing, known as an apnea, can last for up to one minute before the blood oxygen levels reach a critical point where the patient has an arousal and their airway reopens. Most OSA suffers do not remember these arousals however each arousal places extra strain on a patient's heart and destroys the quality of their sleep.

OSA is as prevalent as diabetes or asthma but is an extremely undiagnosed condition. Studies have shown it can lead to significant health problems if left untreated.

The treatment for OSA may include CPAP. CPAP involves the patient wearing a nasal or facemask that delivers positive pressure into the patients airway. This acts as a pneumatic splint and holds the patients airway open to prevent apneas.

2.1 Mechanical Ventilation

A mechanical ventilator is a machine that generates a controlled flow of gas into a patient's airways and is configured to assist patients who are unable to maintain self-sufficient respiration.

Patients generally require mechanical ventilation for three main reasons. These include
1. Damaged or diseased lungs;
2. Insufficient respiratory drive;
3. Inadequate respiratory muscles.

A mechanical ventilator essentially performs the role of the medulla in that it initiates respiration and the diaphragm by expanding and contracting the lungs. A mechanical ventilator may also assist the patient in respiration once the patient begins respirating.

Mechanical ventilators can be sub-categorised into invasive and non-invasive ventilators. Invasive ventilators actually enter the body, whereas non-invasive ventilators perform the function external to the body.

These two sub-categories can be further sub divided into positive and negative pressure devices, referring to the type of pressure that is used to expand the lungs.

In negative pressure devices, a negative gauge pressure is created external to the chest, thus drawing the chest outwards and dilating the lungs, for example as with an iron lung.

In positive pressure devices, a positive gauge pressure is created inside the lungs thus drawing air into the lungs.

Clinical studies have illustrated the benefits that Non-Invasive Positive Pressure Ventilation (NIPPV) has over the other ventilation devices. This includes significantly reducing the number of complications such as infection, no loss of the airway defense mechanism, and reduced need for patient sedation.

NIPPV is a suitable treatment for a wide range of diseases and conditions. These include:
1. Spinal cord injury;
2. COPD;
3. Cystic fibrosis; and
4. Muscular dystrophy.

SUMMARY OF THE INVENTION

One aspect of the invention relates to enhancing the treatment delivery by a device that incorporates all, or most, of the components of a NIPPV system into a single wearable device. For example, the mask and flow generator may be integrated into a mask system worn by the patient. The flow generator may be incorporated into the mask or a headgear configured to support the mask. This aspect provides several advantages over current NIPPV systems.

Another aspect of the invention relates to a patient interface that incorporates a flow generator and provides effective treatment while maintaining or improving patient comfort, including the reduction of pressure points on the patient's face and the reduction of vibration and noise transmittance to the patient, without obstructing the patient's vision.

According to one sample embodiment of the present invention, a system for delivering a pressurized flow of breathable gas to a patient comprises a patient interface configured to contact a wearer's head, the patient interface comprising a frame, a cushion supported by the frame and configured to sealingly connect the patient interface to the patient's face and form a chamber between the frame and the wearer's face, and ~n inlet port in the frame to receive the pressurized flow of breathable gas. A flow generator is configured to generate the pressurized flow and is capable of creating a pressure of about 2-40 cm $H_2O$ in the chamber. A flow generator housing is provided to house the flow generator. The flow generator housing is mounted on the patient interface and configured to reduce the transmission of vibration and/or noise generated by the flow generator to the patient interface.

3. Advantageous Features of the Present Invention 3.1 Reduction in Mask Leakage One advantage is a reduction in mask leakages. Leaks between the patient's face and the mask are a significant issue for NIPPV and may be caused by the force of the air tube pulling on the patient interface, e.g., mask. So by removing the tube this cause of leaks is eliminated.

3.2 Improved Treatment Accuracy

Another advantage is the improvement of treatment accuracy. The impedance and length of the tube imparts a lag in the response and rise time in the pressurised air from the flow generator to the mask. This can reduce treatment efficacy, but by removing the tube this problem is eliminated.

3.3 Increased Useability

Still another advantage is that the system is easier to use and also increases mobility of the patient while they are wearing the device, making it suitable for many applications.

3.4 Reduction in Functional Dead Space

An even further advantage of the present invention associated with the removal of the air tubing is a reduction in the functional dead space of the mask. Functional dead space is defined as the volume of exhaled air that is trapped within the system and that the patient subsequently re-breathes. It is desirable that functional dead space is kept within a safe range, or in the most extreme cases this could lead to the eventual patient suffocation. Current techniques to reduce functional dead space involve minimizing internal volume of the mask to minimize the amount of $CO_2$ that is re-breathed and maximising the vent size and thus air flow through the mask to flush out the trapped $CO_2$. Part of the $CO_2$ that is re-breathed by the patient comes from the exhaled air that is breathed back into the tube. By removing the tube this reduces the physical volume that is available to trap $CO_2$ and hence reduces functional dead space. This has implications for mask design. The first implication is that the internal volume of the mask can be made larger to increase the range of fit for each mask. The second implication is that this could lead to reduced flow requirements. If less $CO_2$ is trapped in the mask, then the required flow rate to remove this $CO_2$ is less. Reducing the flow rate will lead to a reduction in noise created as air rushes through the vents, reduce the power requirements of the pump, and increase patient comfort.

BRIEF DESCRIPTION OF THE DRAWINGS

Sample embodiments of the invention will be described below with reference to the attached drawings, in which:

FIG. 9I schematically illustrates the sample embodiment of the mask of FIGS. 9A-9D including the cover of FIGS. 9E-9H;

FIG. 15 schematically illustrates a vibration model;

FIG. 16 schematically illustrates the loss coefficient versus the Young's modulus for various materials;

DETAILED DESCRIPTION

4. System Design

Figures 1, 2:
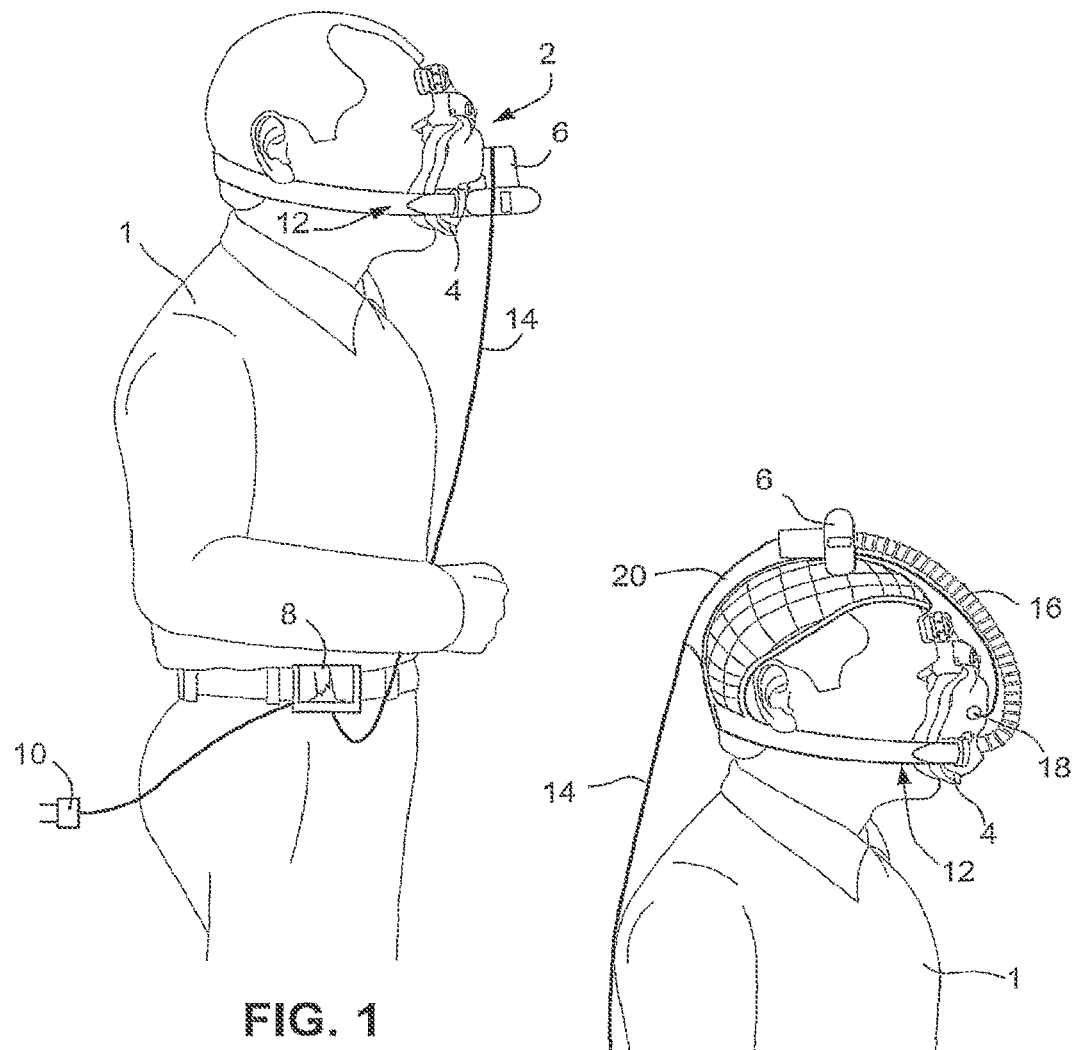
FIG. 1 schematically illustrates a ventilator mask and system configuration according to the present invention.
FIG. 2 schematically illustrates a first sample embodiment of a ventilator mask and system according to the present invention.

Referring to FIG. 1, a NIPPV system according to the present invention can generally be divided into two components. The first component is the user interface 8. The user interface 8 houses electrical components and allows the user 1 to control the system. The second component is the patient interface 2. The patient interface 2 is configured to house a flow generator 6, e.g., a pump, configured to generate a pressurised airflow in a mask 4 and deliver the pressurized flow into the user's airways. It should be appreciated that the mask 4 may be a nasal mask or a full face mask.

A power supply connector 10 may be provided to the user interface 8 to provide power to the user interface 8. The power supply connector 10 may also be configured to charge a rechargeable battery of the user interface 8.

The patient interface 2 may also include a headgear 12 configured to secure the mask 4 to the patient's face so that the mask 4 forms a substantially leak proof seal with the patient's face.

An electrical connector 14 may be provided between the user interface 8 and the patient interface 2. Electrical signals may be provided between the user interface 8 and the patient interface 2 by the electrical connector 14. As shown in FIG. 1, the user interface 8 may be secured to the user's clothing, e.g., a belt. It should be appreciated however that the user interface 8 may be configured to be attached to the user 1 in any manner, for example, by a strap or clip.

The user interface 8 may include a programmable logic controller, or microcontroller, configured to control the operation of the flow generator 6. User controls, such as buttons, dials, etc., may be provided to allow the user to operate the user interface 8. The user interface 8 may include, for example, a display, such as a graphic LCD, a keypad, a motor control, a user interface control, a power supply, an indicator or alarm, such as an audible buzzer and/or LED's.

4.1 First System Configuration Sample Embodiment

Referring to FIG. 2, a NIPPV system according to one sample embodiment of the present invention includes a user interface 8 connected to a flow generator 6 by an electrical connector 14. The headgear 12 may include a headgear power supply support 20 that incorporates a power supply for the flow generator 6. The power supply may be, for example, a battery or batteries. The mask 4 is connected to the flow generator 6 by a tube or conduit 16. A pressure sensor 18 may be provided in the mask 4 to provide signals to the user interface 8. The conduit 16 may include a wire or wires for transmitting signals to and from the user interface 8 and the mask 4.

4.2 Second System Configuration Sample Embodiment

Figure 3:
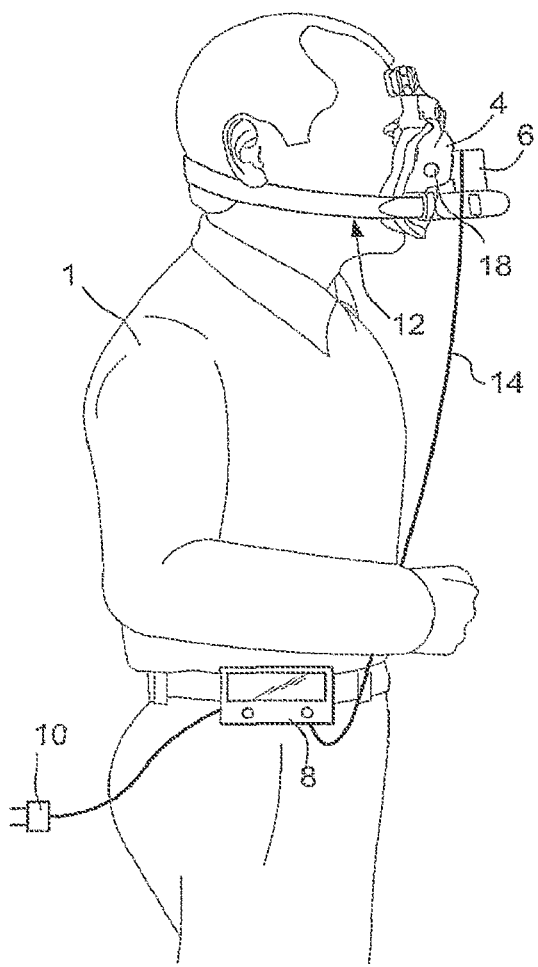
FIG. 3 schematically illustrates a second sample embodiment of a ventilator mask and system according to the present invention.

As shown in FIG. 3, another sample embodiment of the present invention includes a mask 4 configured to engage the face of the patient 1. A headgear 12 is configured to support the mask 4 on the patient's face. A flow generator 6 is incorporated into the mask 4, as will be described in detail below. A user interface 8 is configured to be attached to the patient 1, or the patient's clothing. An electrical connector 14 may be provided between the user interface 8 to provide signals to and from the flow generator 6 to control operation of the flow generator. A pressure sensor 18 may be provided in the mask 4 to provide signals to the user interface 8. The user interface 8 may control operation of the flow generator 6 using signals received from the pressure sensor 18. A power supply connector 10 may be provided to connect the user interface 8 to a power supply. It should be appreciated, however, that the user interface 8 may operate on batteries, including rechargeable batteries.

4.3 Third System Configuration Sample Embodiment

Figure 4:
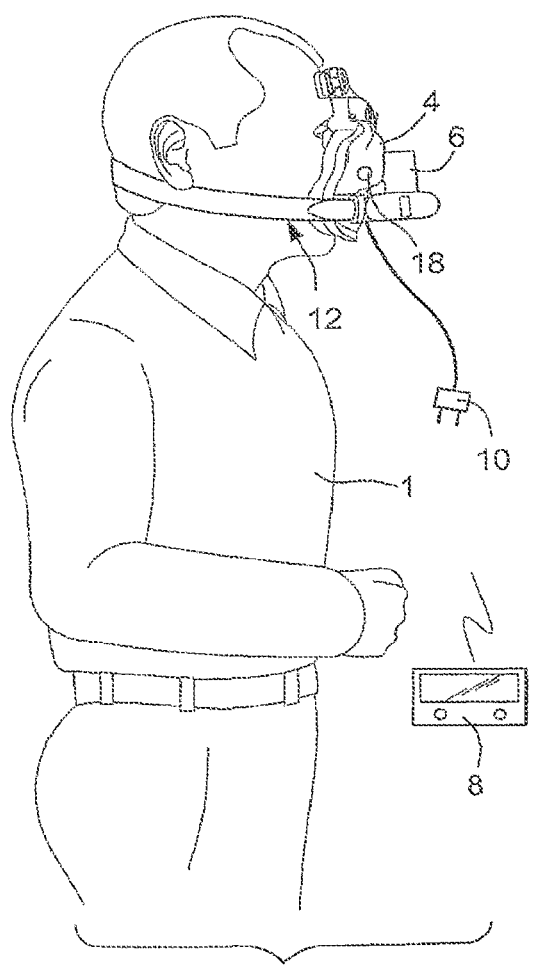
FIG. 4 schematically illustrates a third sample embodiment of a ventilator mask and system according to the present invention.

FIG. 4 illustrates another sample embodiment of the invention. A flow generator 6 is incorporated into a mask 4. The flow generator 6 and the mask 4 are supported by a headgear 12 for sealing contact with the face of the patient 1. A pressure sensor 18 may be provided in the mask 4. A power supply connector 10 may be provided to supply power to the flow generator 6 and the pressure sensor 18. A wireless user interface 8 may be provided to send and receive signals from the pressure sensor 18 and the flow generator 6 to control operation of the flow generator 6. The wireless user interface 8 may include an independent power supply.

4.4 Fourth System Configuration Sample Embodiment

Figure 5:
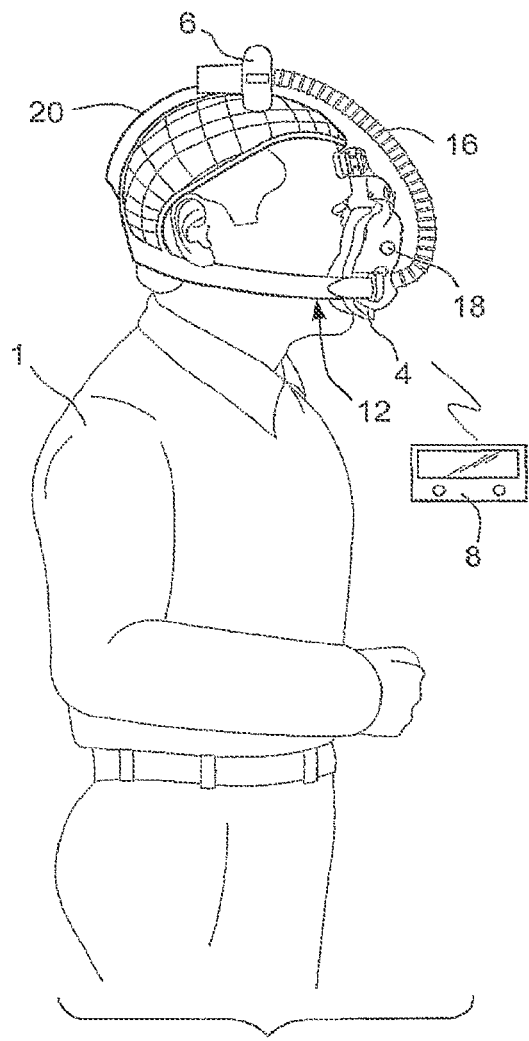
FIG. 5 schematically illustrates a fourth sample embodiment of a ventilator mask and system according to the present invention.

Referring to FIG. 5, a mask 4 is supported for sealing contact with the face of a user 1 by a headgear 12. The headgear 12 may include a power supply support 20 that also may support a flow generator 6. A tube or conduit 16 is configured to supply pressurized air from the flow generator 6 to the mask 4. The headgear power supply support 20 may support a power supply, e.g., a battery or batteries, for the flow generator 6. A pressure sensor 18 may be provided to provide signals indicative of the pressure of the air delivered to the mask 4 to a wireless user interface 8. The user interface 8 may use the signals from the pressure sensor 18 to control the operation of the flow generator 6. The user interface 8 may include a power supply independent from the power supply for the flow generator 6.

4.5 Fifth System Configuration Sample Embodiment

Figure 6:
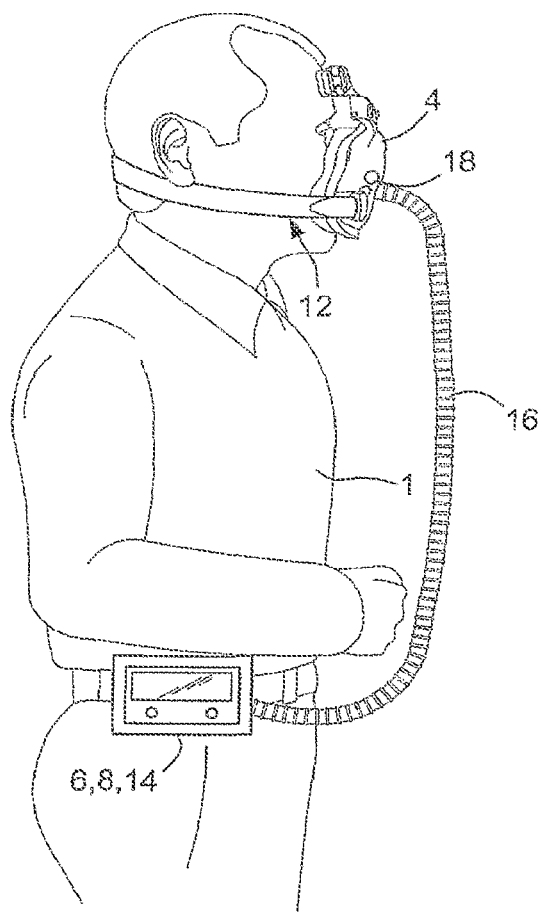
FIG. 6 schematically illustrates a fifth sample embodiment of a ventilator mask and system according to the present invention.

According to another sample embodiment shown in FIG. 6, a mask 4 is supported for sealing contact with the face of a user 1 by a headgear 12. A flow generator 6 is configured to supply pressurized breathable gas to the mask 4. A tube or conduit 16 is configured to deliver the pressurized breathable gas from the flow generator 6 to the mask 4. The flow generator 6 and electrical connection 14 may be incorporated into a user interface 8. The user interface 8 and flow generator 6 may be configured to be attached to the user 1 or the user's clothing, such as a belt. The user interface may receive signals from a pressure sensor 18 provided in the mask 4 and use the signals to control the operation of the flow generator 6. The user interface 8 may be connected to the mask 4 and the pressure sensor 18 by an electrical connector, which may be incorporated into the conduit 16. The user interface 8 may' also receive signals from the pressure sensor 18 wirelessly.

4.6 Sixth System Configuration Sample Embodiment

Figure 7:
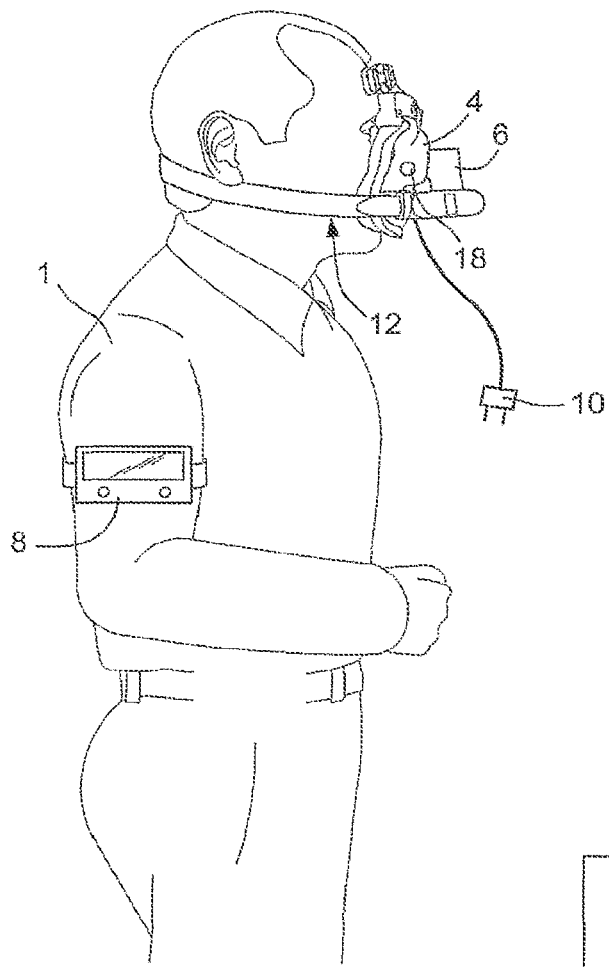
FIG. 7 schematically illustrates a sixth sample embodiment of a ventilator mask and system according to the present invention.

As shown in FIG. 7, a user interface 8 may be supported on an arm of a user 1, for example by a strap. The user interface 8 is configured to receive signals from a pressure sensor 18 provided in a mask 4 supported on the face of the user 1 by a headgear 12. A flow generator 6 may be incorporated into the mask 4. The user interface 8 may receive the signals from the pressure sensor 18 through an electrical connector 14, and control operation of the flow generator 6 through the electrical connector 14. It should also be appreciated that the user interface 8 may communicate with the pressure sensor 18 and the flow generator 6 wirelessly. A power supply connector 10 may be provided to supply power to the flow generator 6.

4.7 Seventh System Configuration Sample Embodiment

Figure 8A:
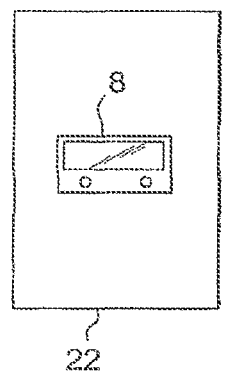
FIGS. 8A and 8B schematically illustrate a seventh sample embodiment of a ventilator mask and system according to the present invention.
Figure 8B:
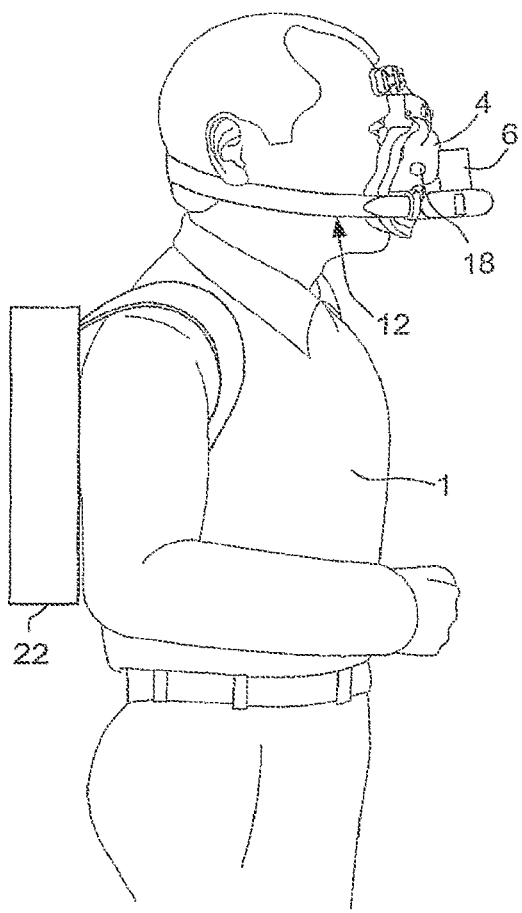

Referring to FIGS. 8A and 8B, a mask 4 is supported for sealing contact with the face of a user 1 by a headgear 12. A flow generator 6 is incorporated into the mask 4 for delivery of pressurized breathable gas to the mask 4. A pressure sensor 18 is configured to provide signals indicative of the pressure at the mask 14. The pressure sensor signals may be delivered to a user interface 8 by an electrical connector 14. The user interface 8 is configured to control the operation of flow generator 6 using the pressure sensor signals. The user interface 8 may be provided in a power supply 22. The power supply 22 may include batteries, including, for example, rechargeable batteries. The power supply 22 may be configured to be carried by the user 1, for example in a manner similar to a backpack. The power supply 22 may provide power to the user interface 8 and the flow generator 6.

4.8 System Configuration Components

According to the sample embodiments described above, the patient interface 2 may delivers the pressurised air flow into the patient's airways and may include some or all of the following components:

Mask,
    Headgear, cushion, etc.;
Flow generator housing;
Flow generator,
    Motor, impeller, volute;
Sensors,
    Pressure;
    Temperature;
    Flow; and
    Volume.

The second component, i.e., the user interface 8 may be configured to control the operation of the flow generator and may include some or all of the following components:

Graphic LCD;
Keypad;
Micro controller;
Motor control;
User interface control;
Power supply;
Audible buzzer;
LEDs.

Figure 9:
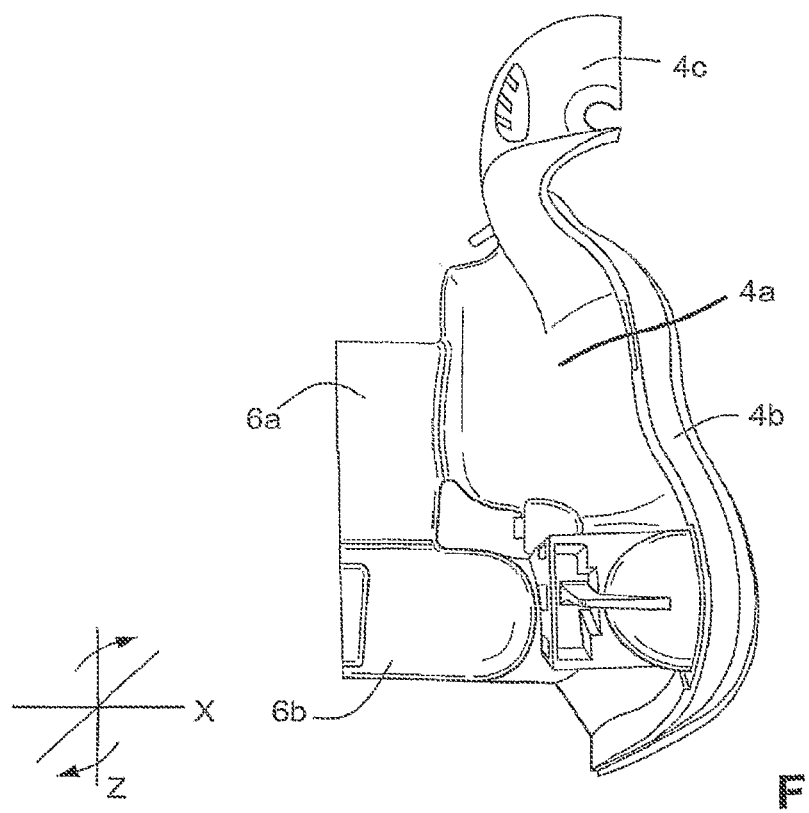
FIGS. 9-9I schematically illustrate a sample embodiment of a mask having a flow generator incorporated therein, wherein FIG. 9A schematically illustrates a front view of a sample embodiment of a mask according to the present invention.
Figure 9A:
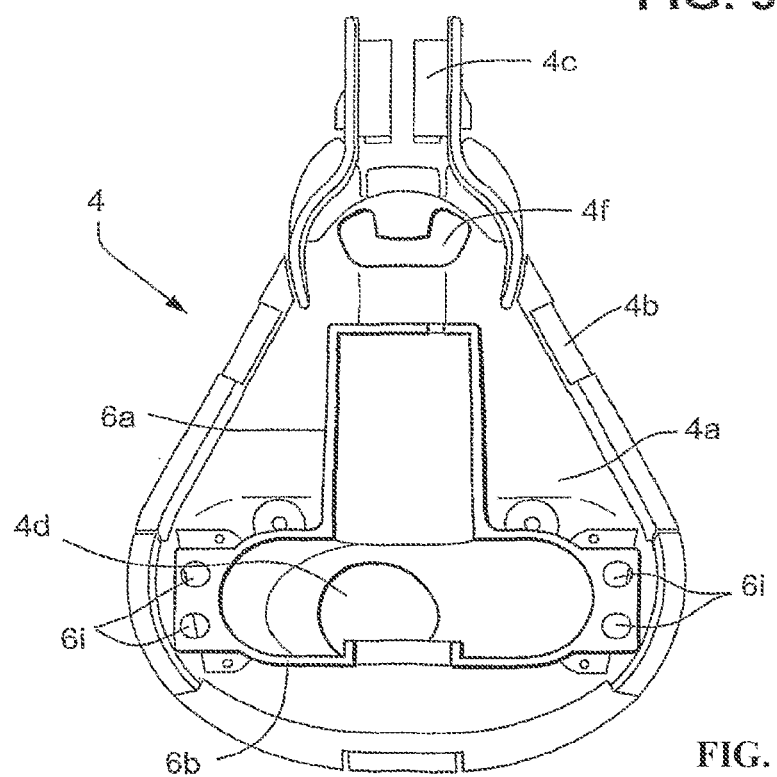
FIG. 9B schematically illustrates a bottom view of a sample embodiment of a mask according to the present invention.
FIG. 9C schematically illustrates a rear view of a sample embodiment of a mask according to the present invention.
FIG. 9D schematically illustrates a top view of a sample embodiment of a mask according to the present invention.
FIG. 9E schematically illustrates a bottom view of a cover for a flow generator of a mask according to FIGS. 9A-9D.
FIG. 9F schematically illustrates a side view of the cover of FIG. 9E.
FIG. 9G schematically illustrates a front view of the cover of FIGS. 9E and 9F.
FIG. 9H schematically illustrates a rear view of the cover of FIGS. 9E-9G.
Figure 9B:
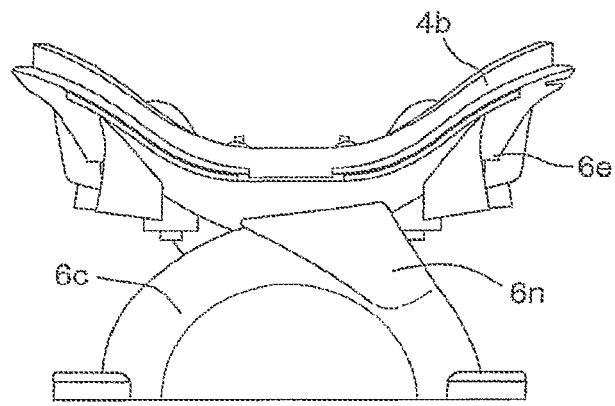
Figure 9C:
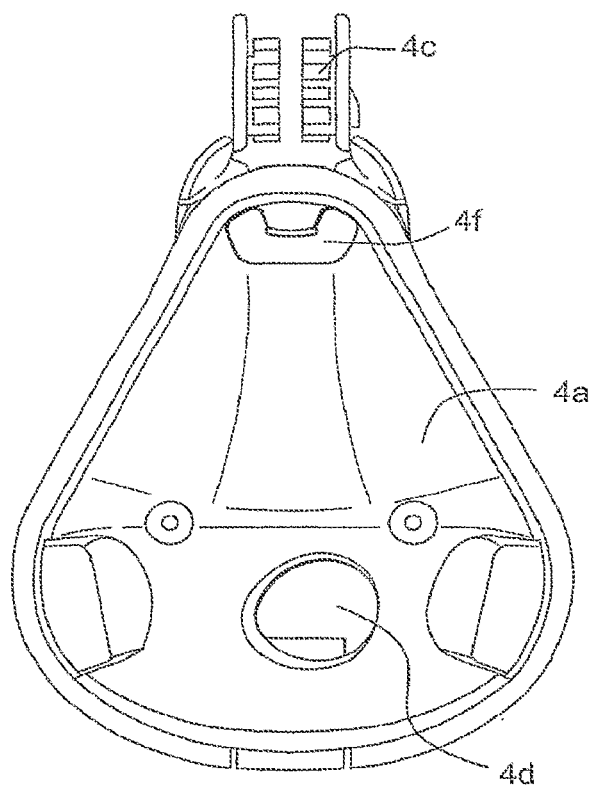
Figure 9D:
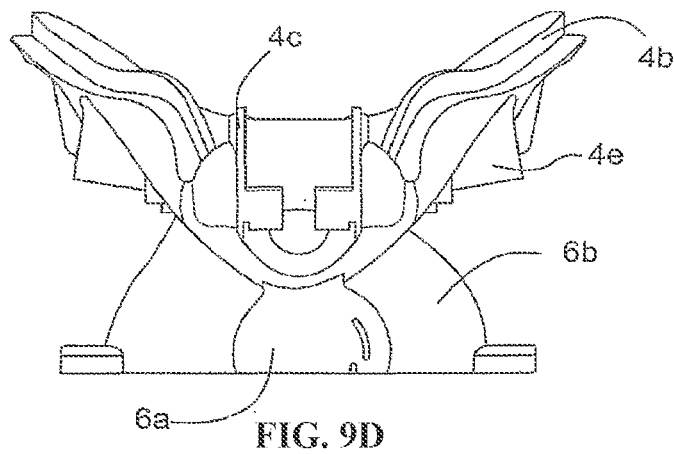
Figure 9E:
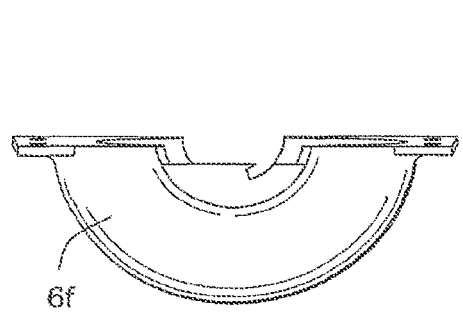
Figure 9F:
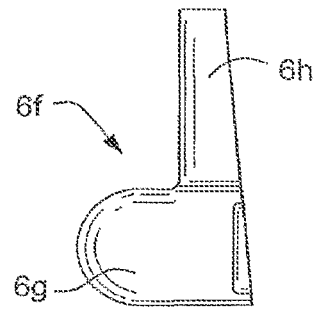
Figure 9G:
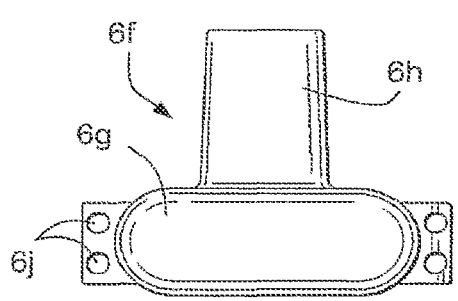
Figure 9H:
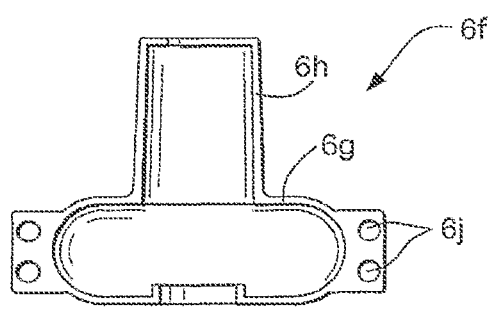
Figure 9I:
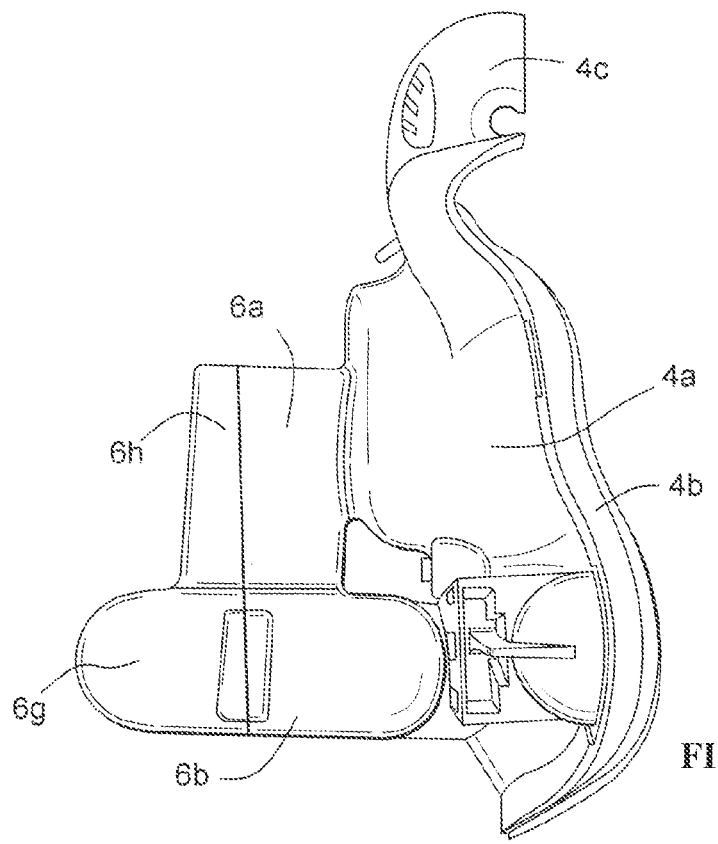

Referring to FIGS. 9-9I, a mask 4 according to a sample embodiment of the invention may include a mask shell 4a and a cushion 4b. The cushion 4b may be formed of a soft material, for example a rubber material, such as a silicone elastomer. The cushion is configured to sealingly contact the face of the user 1 to form an air chamber between the user's face and the mask 4. The shell 4a may be formed of relatively hard plastic, although it should be appreciated that the shell 4a may be formed of the same material as the cushion 4b.

The mask shell 4a may include an extension 4c. A forehead support may be attached to the mask extension 4c to stabilize the mask 4 against the wearer's face once a comfortable, substantially leak proof fit is obtained. The mask shell 4a may also include headgear connectors 4e, including a headgear connector on the extension 4c, to receive straps of the headgear 12 to secure the system to the user's head.

As shown in FIGS. 9-9E, the flow generator 6 may be incorporated into the mask 4. Referring to FIG. 9A, the flow generator 6 may include a motor housing first part 6a and a volute housing first part 6b. The motor housing first part 6a and the volute housing first part 6b are configured to receive the motor and volute of a pump of the flow generator, as discussed in more detail below. The motor housing first part 6a and the volute housing first part 6b may be integrally formed with the mask shell 4a. It should be appreciated, however, that the motor housing first part 6a and the volute housing first part 6b may be formed separately from the mask shell 4a and attached thereto, for example by adhesive or with fasteners, as discussed in more detail below.

Referring to FIGS. 9A and 9B, the volute housing first part 6b includes an outlet 6c that directs the airflow from the flow generator 6 to an inlet 4d in the mask shell 4a. As shown in FIGS. 9A and 9C, the mask shell 4a may include a vent opening 4f that may be covered by an insert (not shown) including apertures for controllably exhausting $CO_2$.

A motor and volute housing second part, or cover, 6f is configured to cover the motor housing first part 6a (part of an upper portion of a housing for the flow generator 6) and the volute housing first part 6b (part of a lower portion of the housing for the flow generator 6), as shown in FIGS. 9E-9H. The cover 6f includes a volute cover part 6g (part of the lower portion of the housing for the flow generator 6) and a motor cover part 6h (part of the upper portion of the housing for the flow generator 6). Apertures 6j may be provided in the volute cover part 6g, as shown in FIGS. 9G-9H, and are configured to mate with apertures 6i formed on the volute housing first part 6b. The cover 6f may be secured to the motor housing first part 6a and the volute housing first part 6b by fasteners (not shown) extending through the apertures 6i and 6j formed in the motor housing first part 6a and the cover 6f, respectively. In the fastened condition, shown in FIG. 9i, the cover 6f and the motor housing first part 6a and the volute housing first part 6b form a housing for the motor, the volute and the impeller, i.e., a housing for the flow generator 6.

Although the motor housing first part 6a and the volute housing first part 6b and the cover 6f have been described as connected by fasteners, it should be appreciated that they may be connected by other mechanisms, such as adhesive or by complementary mating and locking (e.g. snapping) surfaces.

5 System Design Considerations and Approaches 5.1 User Interface 5.1.1 Design Consideration: Useability The system of the present invention is configured to be simple (e.g., intuitive) to use and communicate clearly with the user, both for experienced and inexperienced users.

5.1.2 Design Approach: Usability

To provide a "user friendly system," a significant amount of information may be required to be communicated to the user. This functional requirement may influence the selection of mechanisms to communicate with the user. The system of the present invention may include at least one of the following forms of communication:

Audio, for example a piezo buzzer or some other device that generates an audible signal; and/or
Visual, for example colored LEDs, graphical LCDs or some other display screen.

To achieve clear communication, the communication devices should located in logical and intuitive places. For example, according to one sample embodiment, all of the visual communication devices (e.g., LED's, LCD, etc.) are visible at all times while the system is in use.

5.1.3 Design Consideration: Sanitization and Housing Durability

The user interface 8 may be worn on the patient's body. Because the user interface may be exposed to bodily fluids it should be void of cracks and groves that may harbor infectious particles.

5.1.4 Design Approach: Sanitization and Housing Durability

The user interface may be designed to be void of cracks and grooves that may harbor infectious particles. This can be achieved using such manufacturing techniques, such as overmolding. The user interface housing material should be resistant to oils, dusts, and grease and the ingress of water. The user interface housing should also be durable, with high levels of cut, fade and abrasion resistance. All external connections of the user interface, such as power connections and connections to the patient interface, should be configured to withstand being cleaned.

5.1.5 Design Consideration: Safety

The system of the invention may be configured to communicate with the user if an alarm has been triggered. The system of the invention may also be configured to prevent accidental user input, and to prevent accidental power supply disconnection.

5.1.6 Design Approach: Safety

In one sample embodiment, buttons or other forms of user input of the user interface may be located at a position that they cannot be activated accidentally. In addition, software control could be implemented to ensure that a specific set of buttons must be pushed in series to confirm a setting change.

According to a sample embodiment, the user interface may indicate when an alarm is triggered using at least one of the following techniques:

Audible warning signal, such as a Piezo electric buzzer that generates a clear audible tone,
LEDs to indicate an alarm has occurred; and
Backlight of graphical display illuminates.

To prevent the power supply from accidental disconnection, the power supply connector may include a locking mechanism.

5.2 Mask and Flow Generator Incorporation

As discussed above, the patient interface 2 may include at least one of the mask 4, the headgear 12, the flow generator 6, and sensors (e.g., pressure, temperature, flow and/or volume). In the sample embodiments in which the flow generator is incorporated into the mask, the flow generator housing is configured to mount the flow generator on the mask, secure the connection of the flow generator to the power supply so that it cannot be accidentally disconnected, protect the user from the flow generator inlet and from objects that may enter the air path, and mount any sensor(s), or other electrical devices, to the mask.

Incorporating the flow generator 6 into the mask 4, as disclosed in some of the sample embodiments discussed above, present several design considerations including, but not limited to:

Weight;
Stability;
Noise and Vibration; and
Patient Comfort.

5.2.1 Design Consideration: Weight

The additional weight of a motor and an impeller of the flow generator on the front of the mask may lead to patient discomfort by increasing the forces that are applied to the patient's face while wearing the mask.

5.2.2 Design Approach: Weight

One or some or all of the following techniques may be used to minimize the weight of the patient interface:

Using a low density mask material;
Minimizing wall section thickness;
Hollowing thick sections where strength is not a requirement; and
Minimizing the weight of the flow generator.

A first approach may be to minimize the mask and motor housing thickness to minimize mask weight. For example, according to one sample embodiment, the thickness of the motor housing first part 6a may be 0.5-2.5 mm, for example 1.0-2.0 mm, or for example 1.5 mm. The thickness of the volute housing first part 6b may also be 0.5-2.5 mm, for example 1.0-2.0 mm, or for example 1.5 mm. The motor and volute housing second part, or cover, 6f may also have a thickness of 0.5-2.5 mm, for example 1.0-2.0 mm, or for example 1.5 mm.

5.2.3 Design Consideration: Mask Stability

The additional weight of a motor and an impeller of the flow generator on the front of the mask may also create instability of the mask on the face of the patient, which may cause patient discomfort and reduce the effectiveness of the therapy if the instability prevents substantially leak proof contact between the cushion and the patient's face.

5.2.4 Design Approach: Mask Stability

One approach to providing stability to a mask having an incorporated flow generator is shown in FIGS. 9 and 9I. The flow generator housing, including the motor housing first part 6a, the volute housing first part 6b, and the cover 6f, are provided as close to the mask 4 as possible. The flow generator housing may also be inclined with respect to the mask 4 to reduce the moment of the flow generator 6.

In determining the location of the flow generator 6 on the mask 4, three factors may be considered. The first factor is that as the distance between the patient's face and the center of gravity of the motor and impeller increases, the moment between the flow generator and the mask increases, thus creating greater mask instability. The second factor is the location of the motor and the impeller location should assist in reducing the number of components of the system, such as connecting tubes or conduits, and should not lead to decreased patient comfort, e.g., such as obstructing the patient's vision. The third factor is the weight of the motor and impeller should be evenly distributed across the surface area of the mask cushion that contacts the patient's face. Any localized pressure points would greatly enhance the possibility of patients developing pressure sores in these areas, and the mask should be stabilized so as to reduce, or eliminate, such localized pressure points.

According to sample embodiments of the invention, the location of the flow generator on the mask was selected to be on the front of the mask, located as to be out of the field of vision of the patient to minimize the obtrusiveness of the system. The flow generator was also rotated and positioned such that the centre of gravity of the flow generator is located as close to the patient's face as possible to minimize instability. The flow generator was also located in a position to evenly distribute the additional weight across the entire lower half of the patient's face.

An analysis of the most common facial areas to suffer from pressure sores highlights the areas of the face where bones and other hard tissue are located close to the surface and covered by only small thicknesses of soft facial tissue. This includes areas such as across the bridge of the nose, on the forehead and on the cheekbones. By locating the motor and the impeller in this position, the additional pressure is isolated to areas of the face that can withstand an increase in pressure. Referring to FIG. 9, this position was determined by rotating the motor housing first part 6a and the impeller housing second part 6b about the x and z-axis to achieve the lowest profile possible.

5.2.5 Design Consideration: Noise and Vibration

As the flow generator operates it produces three outputs. The first output is a pressurised airflow. The second and third outputs are side effects of the production of the pressurised airflow, noise and vibration. These side effects may cause patient discomfort, and eventual patient harm if worn for extended periods.

The motor 6d and impeller 6e create noise as they generate the pressurised airflow. This is a consideration because of the close proximity of the motor 6d and the impeller 6e to the patient's face. The close proximity of the motor 6d and the impeller 6e may cause patient discomfort and inhibit patient recovery if it interferes with the patient's rest or sleep.

For a centrifugal fan system, as may be used in the sample embodiments of the system of the invention, there are two primary sources of noise:
1. Tonal or Harmonic Noise; and
2. Blade broadband Noise.

The sound power produced by a centrifugal fan can be estimated by using the following formula:

$$LW = KW + 10 \log 10\, Q + 20 \log 10\, P + BPI + CN,$$

where:
LW=sound power level (dB);
KW=specific sound power level depending on the type of fan;
Q=volume flow rate (cfm);
P=total pressure (inches of $H_2O$);
BPI=blade frequency increment; and
CN=efficiency correction (because fans that are operated off their optimum flow conditions get noisier).

5.2.5.1 Tone or Harmonic Noise

The first component of the noise emitted by the flow generator is referred to as tone or harmonic noise and is due to the rotation of the impeller blades past a fixed position. The specific frequency of this noise is known as the blade pass frequency (BPF). The BPF is equal to the number of blades N times the Revolutions Per Minute (RPM) of the rotor, as defined by the formula:

$$BPF = N \cdot RPM$$

Figure 11:
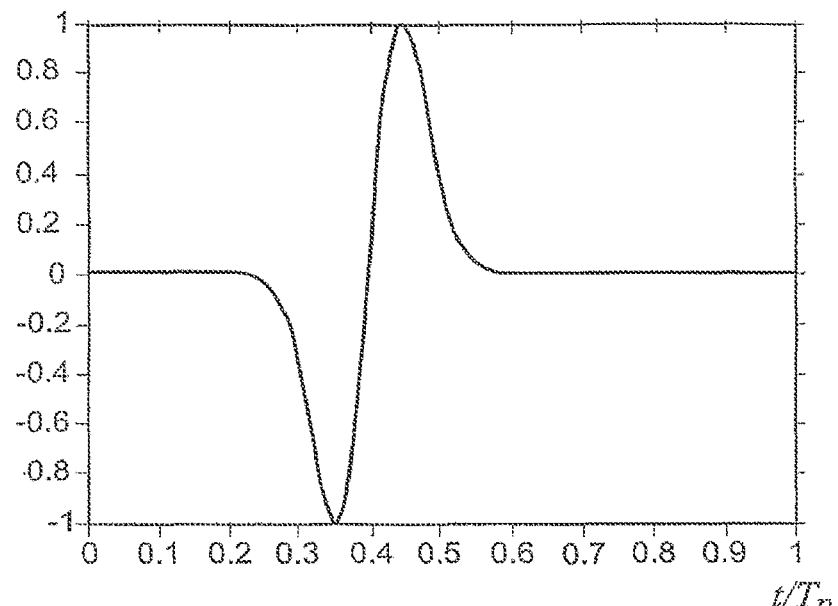
FIG. 11 schematically illustrates the frequency output from a single blade impeller.
Figure 12:
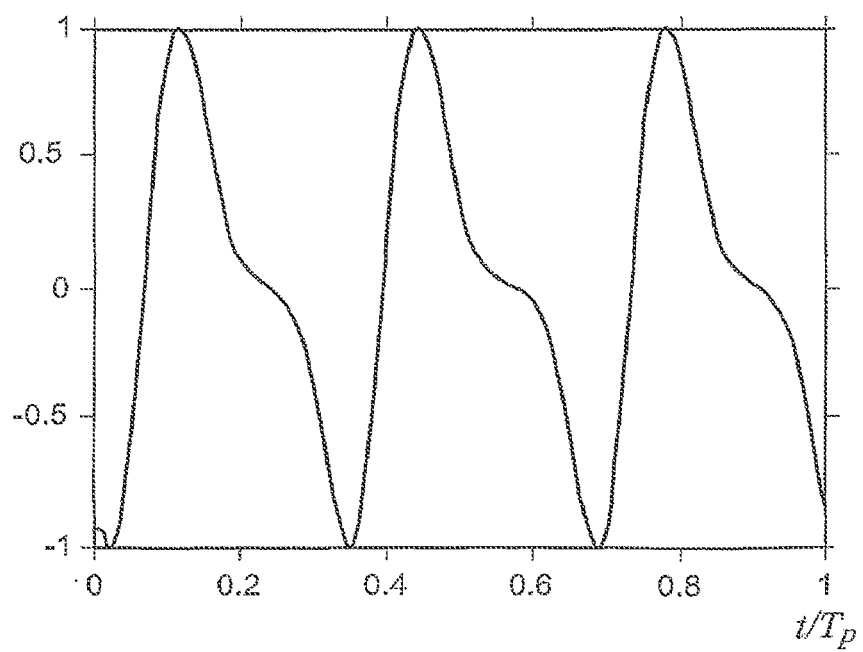
FIG. 12 schematically illustrates the frequency output from a three blade impeller.

The tone or harmonic noise is a problem for centrifugal fans and influences their design. The frequency output of a single and a three blade impeller are pictured in FIGS. 11 and 12, respectively, where the period of one revolution is Tp.

5.2.5.2 Broadband Noise

Figure 13:
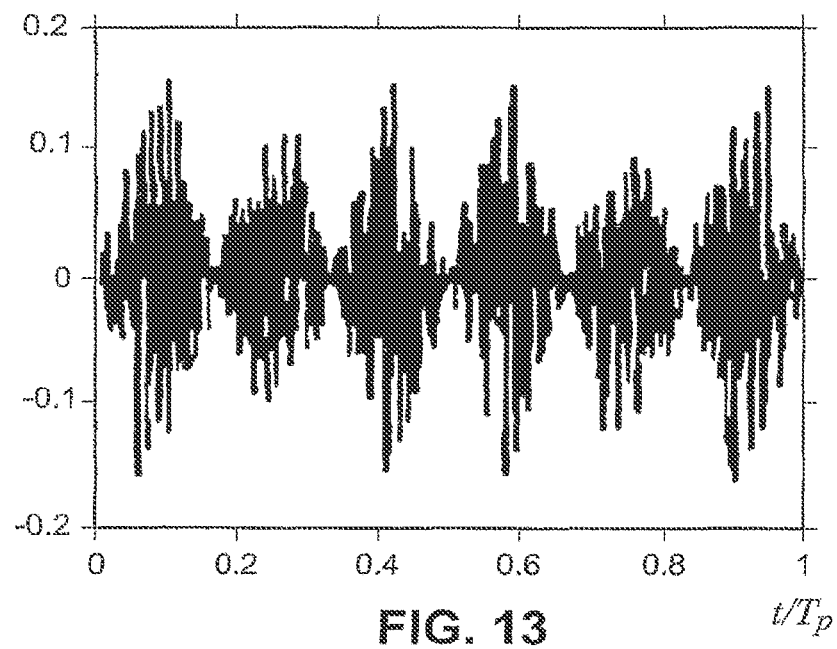
FIG. 13 schematically illustrates broad band noise from a centrifugal fan.

The second component of the noise emitted by a centrifugal fan system is broadband noise. Broadband noise is the random non-periodic signal that is caused by the turbulent flow of air over the blades. An example of a broadband noise that is typical of a rotating impeller is shown in FIG. 13. As shown in the figure, the envelop of the broadband noise varies periodically rather then the actual signal.

5.2.5.3 Total Noise

Figure 14:
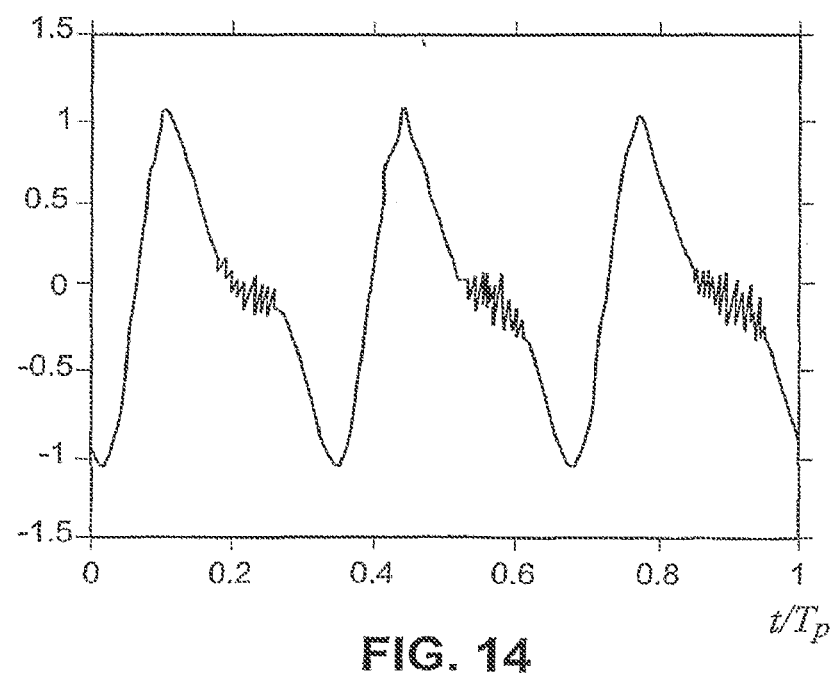
FIG. 14 schematically illustrates total noise produced by a centrifugal fan.

The sum of the blade broadband and tone noise is shown in FIG. 14.

5.2.6. Design Approach: Noise and Vibration

The majority of noise sources can be attributed to vibrating surfaces. Therefore, vibration control is an aspect of noise reduction.

5.2.6.1 Sound Control

To sound proof the mask and the motor housing there are two different techniques that may be used, alone or in combination: noise reduction and noise absorption. A third technique, including the use of a soft joint, may also be used.

5.2.6.2 Noise Absorption

Figure 10:
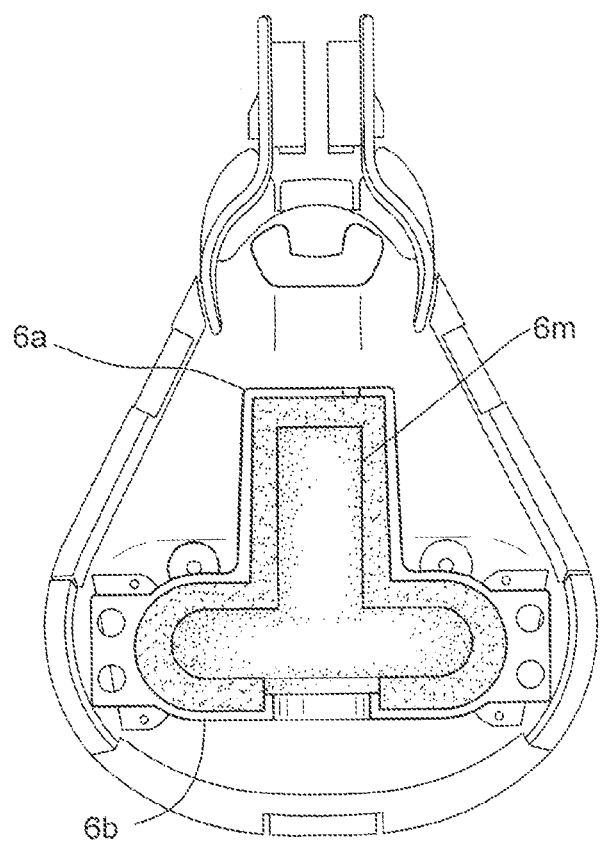
FIG. 10 schematically illustrates a mask and flow generator according to a sample embodiment of the present invention.

Noise absorption operates by transforming the sound wave into another form of energy and acts to suppress the sound. As shown in FIG. 10, to achieve this the motor housing, including the motor housing first part 6a, the volute housing first part 6b and the cover 6f, is designed to allow the insertion of a layer of noise absorbing material 6m, such as open celled polyurethane (or other suitable substance) foam, between the motor 6d and the volute 6c and the housing. Open cell foam is an effective sound barrier as the sound is forced to travel through the different layers of the material with different densities, thus dampening the sound.

15 5.2.6.3 Noise Reduction

The second technique that may be used is noise reduction. Noise reduction includes placing a physical barrier to prevent the transmission of sound. In this situation, the physical barrier is the actual motor housing (i.e., the motor housing first part 6a, the volute housing first part 6b and the cover 6f) and this reflects the sound, for example back into the noise absorbing material 6m. The amount of noise reduction that is possible can be directly correlated to the mass of the physical barrier, hence there will be a trade off between noise reduction and weight issues as discussed previously. The depiction in FIG. 10 shows one sample embodiment of the invention.

5.2.6.4 Soft Flexible Joint

Figure 18:
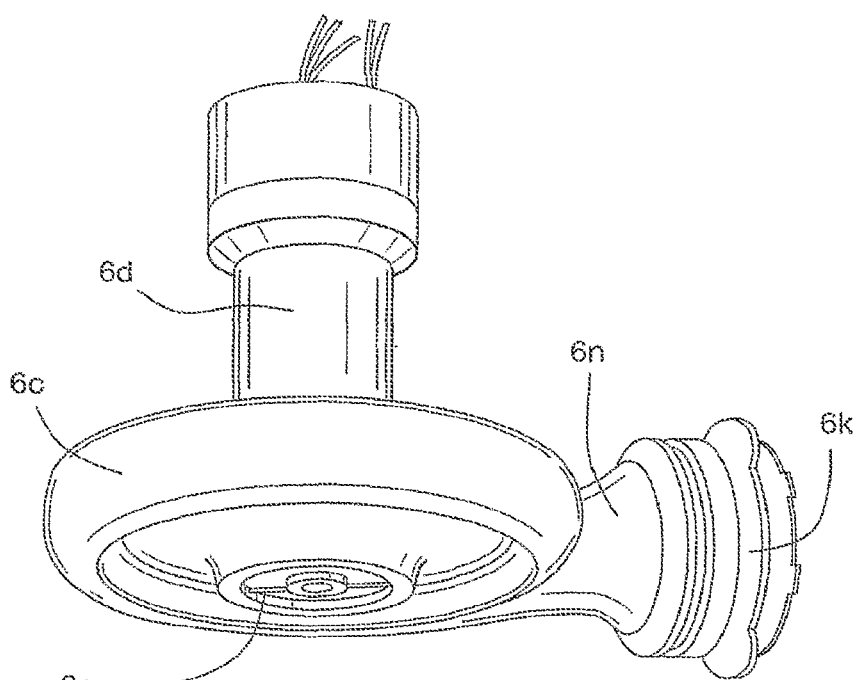
FIG. 18 schematically illustrates a pump of a flow generator according to a sample embodiment of the present invention.

Another approach is shown in FIG. 18. The outlet of the volute housing first part 6b connects to the mask inlet 4d by a soft and flexible joint 6k, for example a gusset or a grommet. The soft and flexible joint 6k is configured to connect the air path from the flow generator 6 to the mask 4. The soft and flexible joint 6k also acts to isolate and dampen the vibration and prevent the vibration form being transferred into the motor and impeller housing and the mask.

5.2.6.5 Vibration Control

Vibration control can be achieved by using three different techniques, isolation, damping and avoiding resonance.

5.2.6.6 Vibration Isolation

A proportion of the noise produced by a centrifugal fan system, which may be used as a flow generator in system according to the invention, can be attributed to vibration. Noise is produced when vibration from one source is transferred to another system that is a better noise radiator than the previous source. In a centrifugal fan system this occurs when the vibration of the motor and impeller is transferred to the flow generator housing and mask. This transfer causes the system to act almost as a speaker. Vibration isolation is thus useful in minimizing noise output.

It is possible to minimize the transmission of vibration from one structure to the next structure by placing an elastic material between the two structures. The elastic materials are often referred to as vibration isolators and have material properties that make them suitable for such a purpose.

According to Tandon N., Noise-reducing Designs of Machines and Structures, Siidhanii, Vol. 25, Part 3, June 2000, pp 331-339, vibration isolation can be understood from the analysis of an ideal, linear, single degree of freedom system in which the isolator is represented by the parallel combination of a massless spring and a damper, as shown in FIG. 15.

The transmissibility of a substance is defined as the ratio of the amplitude of the force transmitted to the supporting structure to that of the exciting force, and can be expressed by the formula:

$$T = \{[1+(2\zeta r)^2]/[(1-r^2)^2+(2\zeta r^2)^2]\}^{1/2},$$

where T is the transmissibility, $\zeta$ is the damping ratio and r is the ratio of the excitation frequency to the natural frequency of the spring mass system. When T is less then one then the system is in isolation. Hence the system is in isolation when $r > 2^{0.5}$. This means that for a substance to be an effective isolator its stiffness must be such that the mounted resonance frequency is less then 0.7 times the minimum forcing frequency. If r is near 1 then this could lead to the vibration being amplified rather then attenuated.

While this model provides an insight into vibration isolation it is not a completely accurate description of vibration in real world circumstances. Vibrating bodies rarely vibrate only vertically and real springs are not massless. However, the model shown in FIG. 15 is useful for understanding the dynamics of vibration transfer.

Many vibration isolators are commercially available and are generally metallic (coil springs or some other form of flexural configuration) or elastomeric resilient elements. Elastomeric elements are suitable for using is situations where vibrations are caused by shear, torsion, compression modes or any combination of these. The loss coefficient versus Young's modulus for various elastomers and other materials is shown FIG. 16.

5.2.6.7 Vibration Dampening

Three general properties may be used to describe the noise characteristics of a structure. These properties include mass, stiffness and damping. Mass and stiffness are associated with the storage of kinetic and shear energy, respectively, whereas damping is associated with the dissipation of energy. Damping is the process by which sonic vibrations are converted to heat over time and distance. Damping results in the decay of unforced vibrations and leads to the reduction in the amplitude of resonance frequency for an object subjected to steady excitations. The damping capacity, $\psi$, of an element is defined as the ratio of energy dissipated per cycle to the energy present in the system. The term used to specify material damping is the loss factor, $\eta$, which may be determined according to the following formula:

$$\eta = (\psi/2\pi) = 2\zeta.$$

Several methods may be used to dampen sound. A first method is to use a high-density soft material, such as lead. The softness and high density combine to dampen the noise rather then transmit it.

Another method is to place material of different densities in the path of the sound waves. The sound waves are forced to travel through the different densities thus reflecting and dampening the sound. This is why open cell foam is such an effective sound dampener 15 5.2.6.8 Avoiding Resonance Resonance is defined as the tendency for a system to oscillate with high amplitude when excited by energy at a certain frequency. Therefore, when designing a structure to minimize the transmission of sound, it is desired that the resonant or natural frequency does not correspond to the frequencies of the excitation forces. This may be a consideration when selecting the final production material and the effect should also be considered when testing different prototype configurations. For an object of a simple geometry, its resonant frequency F may be determined according to the following formula:

$$F = 0.5\pi(\text{stiffness}^{0.5}/\text{mass}^{0.5}).$$

In order for NIPPV therapy to be effective, the patient may e required to use the system for several hours, during which time the patient may be sleeping. In order to allow the patient to use the system for such a time, user comfort should be a consideration. One of the issues for patients wearing a respiratory mask is that it does not inhibit their primary senses, for example sight. It is therefore desirable that the location of the flow generator on the front of the mask does not impinge the patient's field of vision.

Another issue of patient comfort is the weight of the flow generator and mask when these components are incorporated. This consideration was previously discussed with respect to the mask and flow generator weight and the stability of the mask and flow generator when worn by the patient.

5.2.8 Design Approach: Patient Comfort

Figure 17:
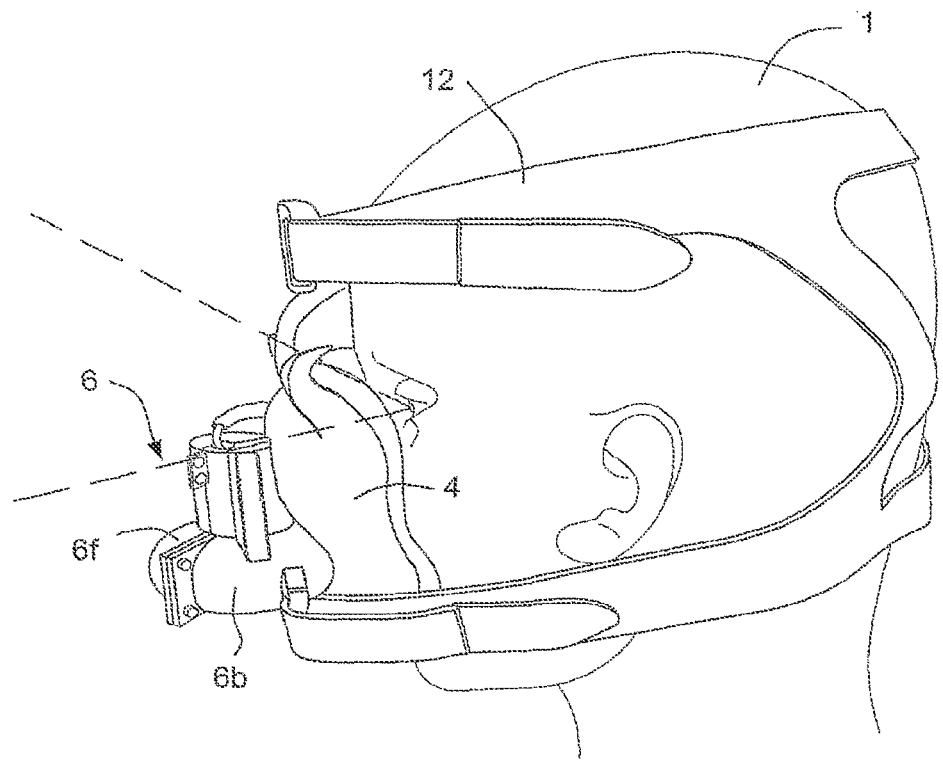
FIG. 17 schematically illustrates a mask and flow generator according to a sample embodiment of the present invention.

One sample method for preventing the pump from impinging on the patient's field of vision is to locate the pump in such a way that it is out of the patients field of vision. According to one sample embodiment shown in FIG. 17, the flow generator is located in relatively the same vertical position as the patient's nose.

5 6 Flow Generator 6.1 Pump

The flow generator 6 is configured to generate the pressurized flow of respiratory gas. The flow generator 6 may include a motor 6*d*, an impeller 6*e* and a volute 6*c*. The motor 6*d*, the impeller 6*e* and the volute 6*c* may be referred to as a pump.

6.1.1 Motor

The motor 6*d* may be a brushless DC (BLDC) motor. A BLDC motor has advantages over DC motors including brushes. One advantage is that the BLDC motor does not require brushes. The BLDC motor can operate at higher maximum speeds and is far less likely to create sparks. This advantage assists in the safe delivery of oxygen. As oxygen is extremely flammable, the creation of sparks is a safety issue.

BLDC motors also require less maintenance because there is reduced frictional contact. BLDC motors also typically operate at cooler temperatures, increasing the lifespan of the internal components. BLDC motors are also more efficient than DC motors with brushes, with a typical efficiency of 85-90% compared to brushed motors that at best deliver an efficiency of 80%. BLDC motors also provide more precise speed control. This is a desirable advantage for the system of the present invention because it enables the system to deliver accurate and effective treatment.

6.1.2 Impeller and Volute

The impeller 6*e* is driven by the motor 6*d* to generate the pressurized flow of respiratory gases. The impeller 6*e* may be a rotating disk that has a set of veins that, when rotated, produce centrifugal force within the volute 6*c*. The volute 6*c* is the stationary housing that encompasses the impeller 6*e* and collects, discharges and recirculates the air entering the pump. As shown in FIG. 18, a soft joint 6*k* may be provided at the volute outlet 6*n* to seal the connection between the volute outlet 6*n* and the mask inlet 4*d*. The soft joint 6*k* may be a silicone grommet or gusset.

6.2 Sensors

In the sample embodiments of the system of the present invention, sensors may be incorporated into the patient interface 2 to measure at least one of the following:

Pressure;

Volume;

Flow; and

Temperature

To measure pressure, a pressure sensor(s) requires access to space where the pressure is to be measured. In the sample embodiments of the system of the present invention, this is in the air path or inside the mask.

Figure 19A:
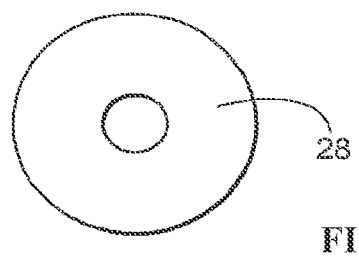
FIG. 19A illustrates an exemplary orifice plate for an obtrusive-flow sensor usable with sample embodiments of the present invention.
Figure 19B:
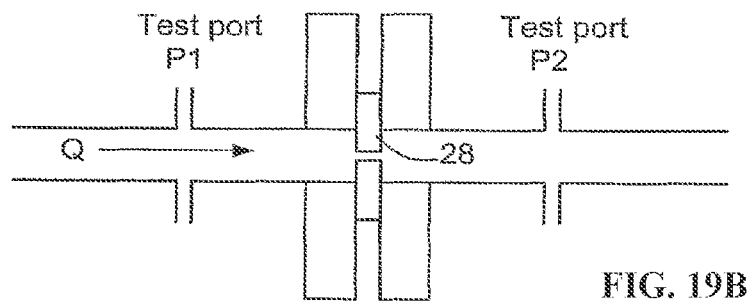
FIG. 19B schematically illustrates operation of an obtrusive-flow sensor usable with sample embodiments of the present invention.

In one sample embodiment, an obtrusive flow sensor may be used to measure flow. An obtrusive-flow sensor operates by placing a small obstruction in the flow and measuring the pressure drop across the obstruction. The obstruction is commonly known as an orifice plate 28 (FIGS. 19A and 19B). According to the present invention, an orifice plate 28 may be provided in an outlet 6*n* of the volute 6*c*, prior to the joint 6k (FIG. 18). It should also be appreciated that the flow sensor may be provided in the joint 6k.

FIGS. 19A and 19B demonstrate the implementation of an obtrusive-flow sensor. When fluid flows through the system, a pressure P1 is measured at a test port on one side of the orifice plate 28. The fluid then flows through the orifice and a lower pressure P2 is measured at a test port on the other side of the orifice plate 8. The flow Q through the orifice plate 8 is directly proportional to the square root of the drop in pressure, and may be defined by the equation:

$$Q = k\sqrt{(P1-P2)}$$

where:
Q=flow in gallons/minute (gpm);
k=is the constant that is determined by the orifice plate;
P1=is the higher pressure in front of the orifice; and
P2=is the lower pressure behind the orifice.

Volume can then be determined by integrating flow with respect to time.

An example of a pressure sensor that could be used in one sample embodiment is the MPXV 5004G pressure sensor manufactured by Freescale Semiconductors. An advantage of the MPXV5004G series is that it is designed for a wide range of applications, including those employing a microcontroller with analog to digital outputs. The pressure range of this sensor also matches required pneumatic performance for most NIPPY therapies with a pressure range of 0 to 40 cm $H_2O$.

The user interface 8 may be configured to receive signals from pressure sensors at the test ports on the sides of the orifice plate 28. The user interface 8 may be configured to calculate the volume and flow of the pressurized gas. The user interface 8 may also control the operation of the motor 6d to deliver the pressurized gas flow at a desired pressure and volume. For example, the NIPPV therapy may be a Continuous Positive Airway Pressure (CPAP) therapy, a Variable Positive Airway Pressure (VP AP) therapy, or a Bi-level Positive Pressure Airway Pressure (BiP AP) therapy.

7 Patient Interface 7.1 First Patient Interface Sample Embodiment

Figure 20:
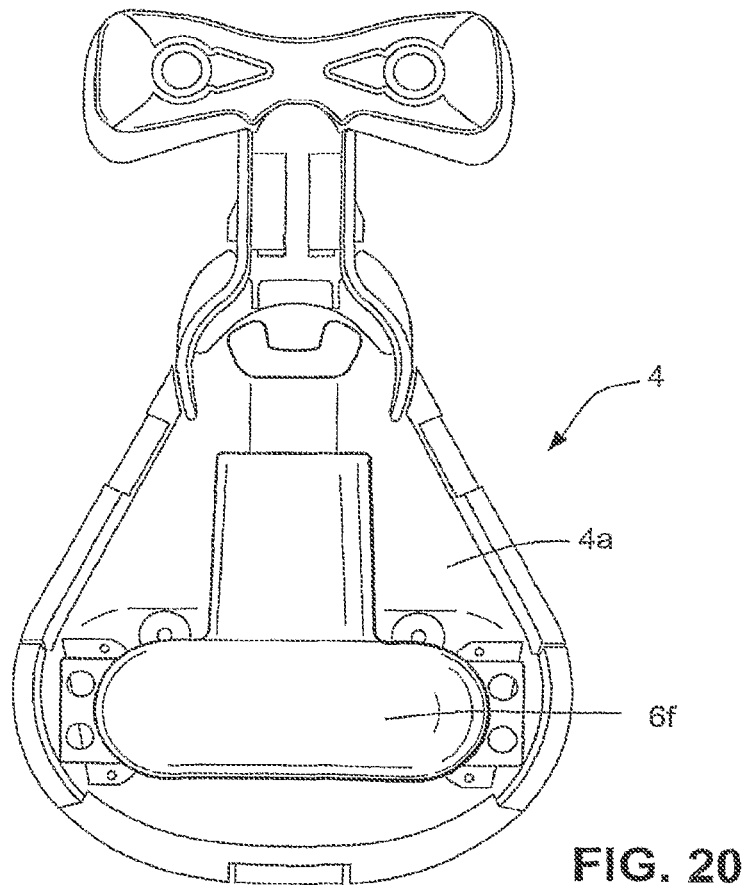
FIGS. 20 and 21 schematically illustrate a mask and flow generator according to a sample embodiment of the present invention.
Figure 21:
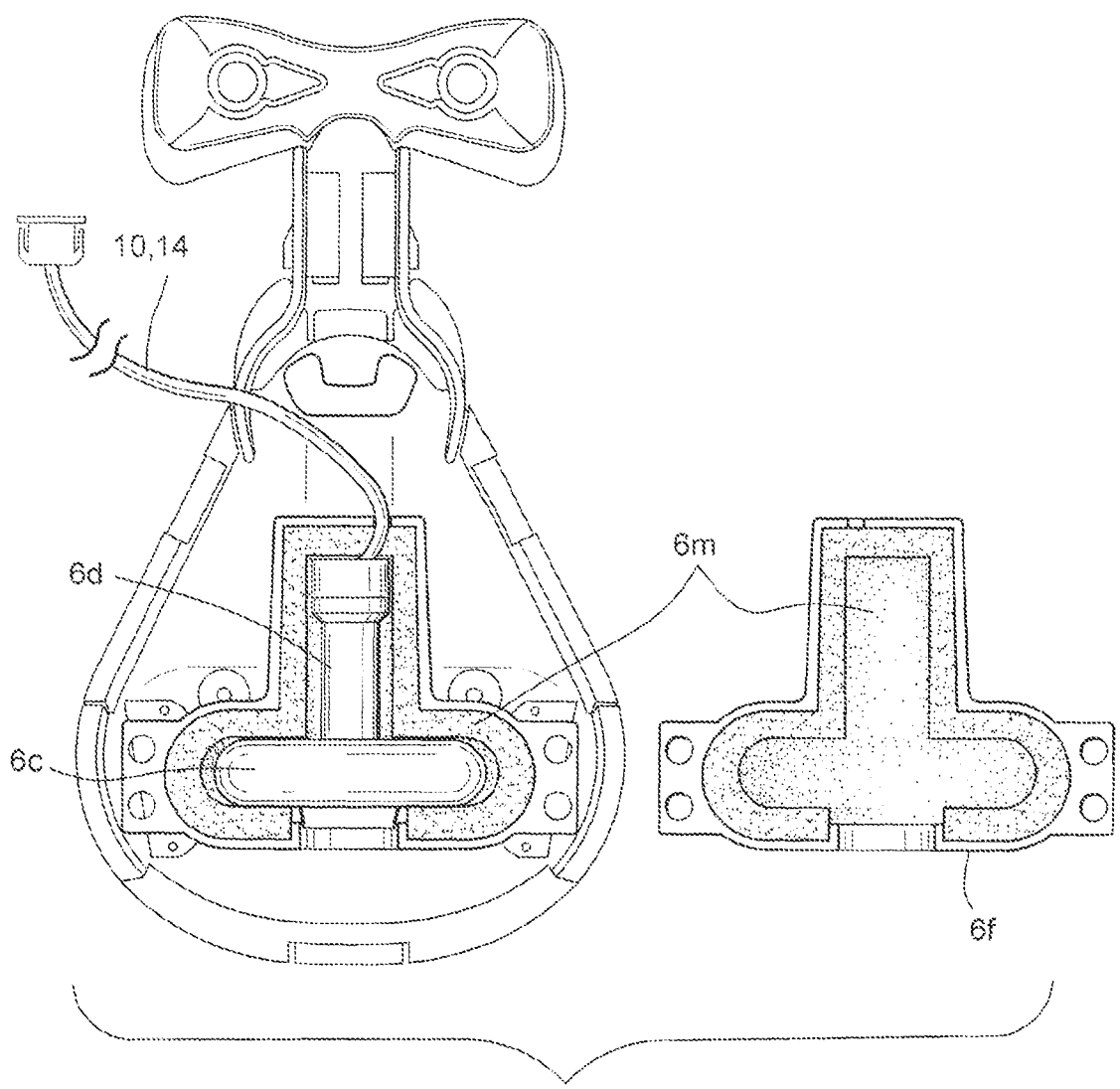

Referring to FIGS. 20 and 21, a patient interface according to a first sample embodiment of the invention includes a mask 4 having a mask shell 4a in which a portion of a pump housing is integrated. The pump housing includes the motor housing first part 6a and the impeller housing first part 6b. The other portion of the pump housing includes the cover 6f which is attached to the mask shell 4a to enclose the pump. As shown in FIGS. 20 and 21, power to the motor 6d may be provided by an electrical connector 14 connected between the user interface 8 and the mask 4, or from a power supply connector 10 that may be connected to a power supply separate from the user interface 8.

Noise absorbing material 6m may be provided in the pump housing, both in the motor housing first part 6a and the impeller housing first part 6b incorporated in the mask shell 4a and in the cover 6f. The noise absorbing material 6m may be, for example, a 5 mm layer of polyethylene foam. The foam is configured to support the pump, prevent vibration transmission 20 and dampen noise emitted from the pump.

7.2 Second Patient Interface Sample Embodiment

Figure 22:
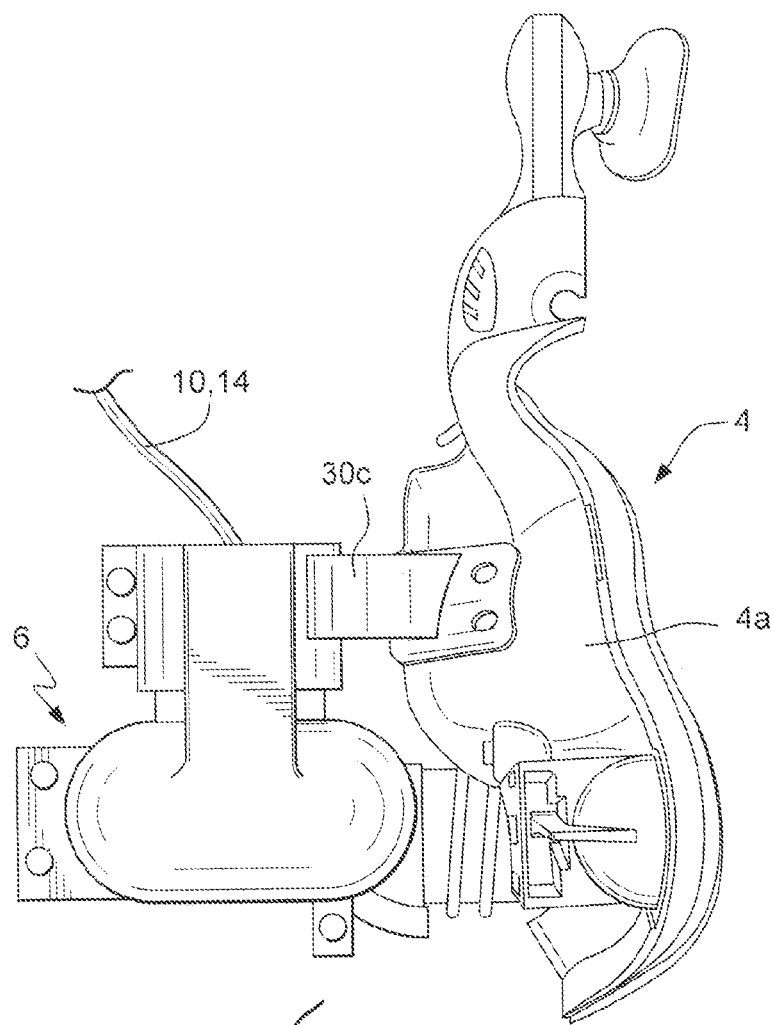
FIGS. 22-26 schematically illustrate a mask and flow generator according to another sample embodiment of the present invention.
Figure 23:
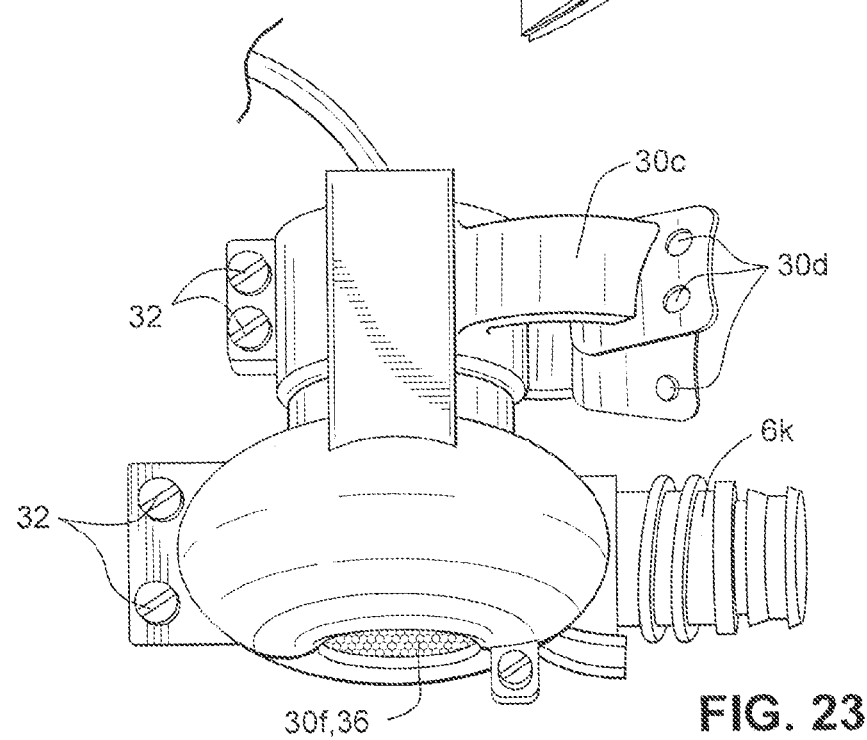
Figure 24:
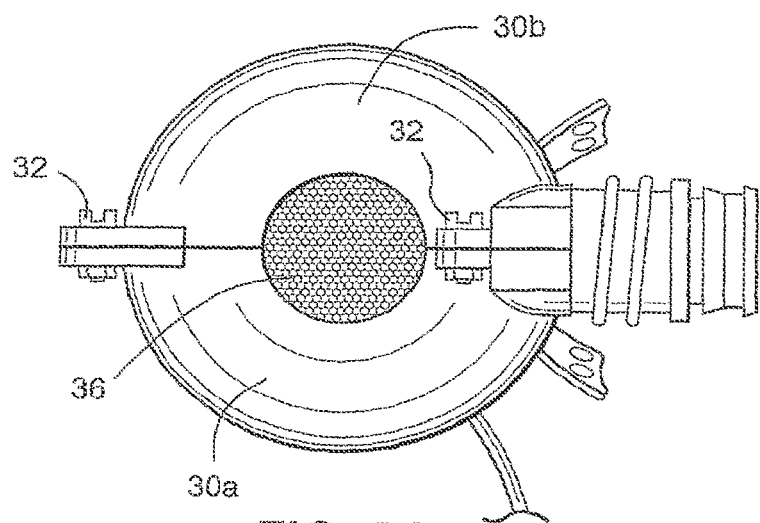

Referring to FIGS. 22-25, a patient interface according to another sample embodiment includes a pump housing 30 formed of two parts 30a, 30b. As shown in FIG. 24, the first and second parts 30a, 30b of the pump housing 30 are connected together, for example by fasteners 32, such as 4 mm plastic nut and bolt sets, to form the pump housing 30.

Referring to FIGS. 22 and 23, the first and second parts 30a, 30b each include a support arm 30c. The support arms 30c include apertures 30d configured to receive fasteners that attach the pump housing 30 to the mask shell 4a. The pump housing 30 is also attached to the mask shell 4a at the mask inlet 4d by a soft joint 6k, e.g., a flexible gusset, that connects the outlet of the pump housing 30 to the mask inlet. The soft joint 6k connecting the pump housing outlet to the mask inlet may be configured to deliver the required vibration isolation properties.

Figure 25:
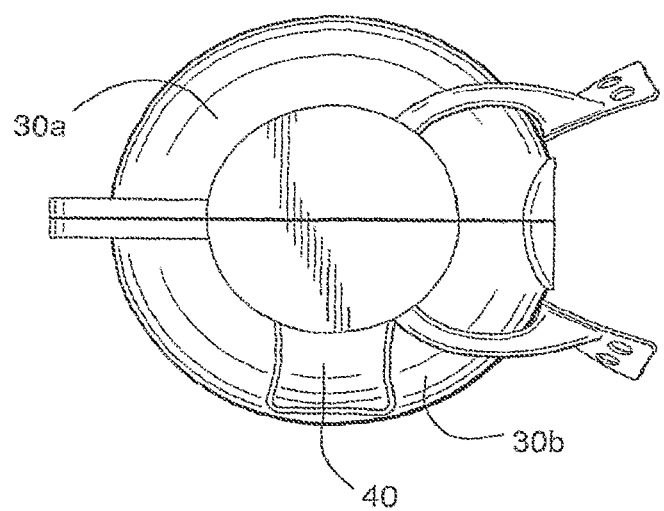

One part of the pump housing 30 houses a pressure sensor 40, as shown in FIG. 25. Although the pressure sensor 40 is shown housed in the second part 30b, it should be appreciated that the pressure sensor 40 may be supported in the first part 30a.

The techniques of noise dampening and vibration isolation used in the first sample embodiment of the patient interface may also be used in the second sample embodiment of the patient interface. In the second sample embodiment, however, the space between the interior wall of the pump housing 30 and the motor and impeller may be increased to allow the insertion of noise absorption and reflection foam. This foam not only provides the sound damping qualities used in the first sample embodiment of the patient interface, but it also provides additional attenuation and reflection due to the high density layer laminated onto the outer wall.

Figure 26:
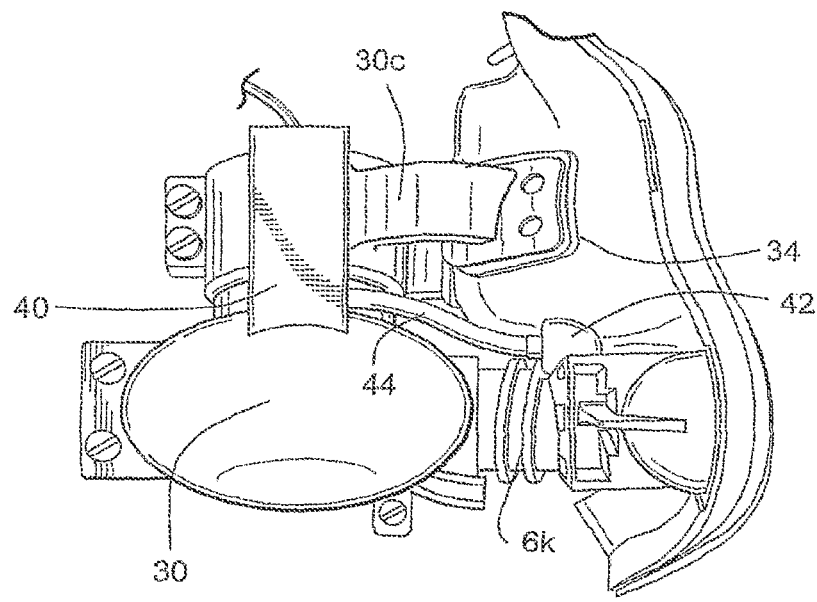

Referring to FIG. 26, a soft joint 34 may be provided between each support arm 30c and the mask shell. The soft joint 34 may be, for example, an elastomeric silicone rubber. As the pump housing 30 of the second sample embodiment is not partially integrated with the mask shell and is formed separately, the use of the soft joints 34 provide an opportunity to isolate the vibrations caused by the pump of the flow generator even further.

Figure 27:
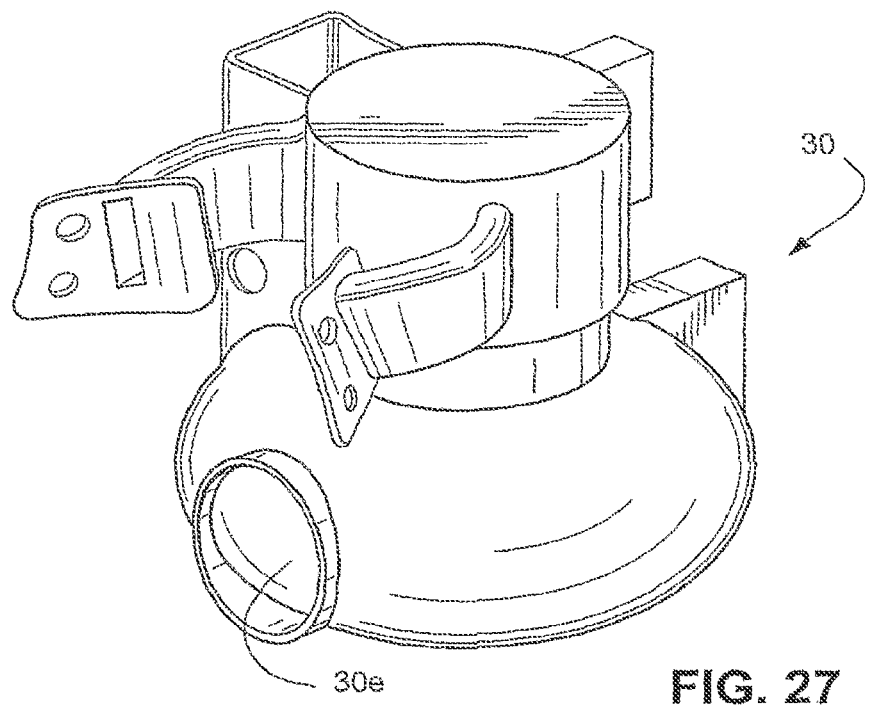
FIG. 27 schematically illustrates a flow generator housing according to another embodiment of the present invention.

Another technique used to minimize the transmission of vibration from the pump housing to the mask is the design of the support arms 30c that attach the pump housing to the mask. In the second sample embodiment, two support arms 30c are used to attach the pump housing 30 to the mask. However, it should be appreciated that more or less supporting arms 20c between the housing and the mask may be provided. It should also be appreciated that the pump housing 30 may be formed as a fully integrated structure, as shown in FIG. 27. As the majority of vibrations for this system occur in a horizontal plane, forming the pump housing as an integrated structure allows the base of the pump housing the freedom to move and not transmit this vibration directly into the mask.

The inlet 30f and the outlet 30e of the pump housing 30 may require safety features to prevent harm to the patient. As shown in FIG. 23, a protective screen 36, for example a fine aluminum mesh, may be provided to cover the inlet 30f. The outlet 30e may also be covered by a protective screen. The protective screen 36 over the inlet 30f prevents the user from inserting a finger into the pump housing 30 and contacting the impeller as it rotates. The protective screen over the inlet 30f may also prevent debris from being drawn into the pump housing 30. The protective screen over the pump housing outlet 30e may prevent debris from being introduced into the mask with the pressurized flow.

Another feature of the second patient interface sample embodiment is the inclusion of a housing to hold a pressure sensor. This is located on the flow generator housing.

As is shown in FIG. 26, the pressure sensor 40 is configured to determine the pressure in the mask 4. A pressure port 42 is formed in the mask 4 and a tube 44 connects the pressure sensor 40 to the pressure port 42. Accordingly, the combination of the pressure port 42, the tube 44, and the pressure sensor 40 spans from the flow generator to a wall of the patient interface. Thus, the pressure sensor 40 is configured to determine the pressure of the flow received by the patient. This configuration provides a more accurate pressure measurement than current systems in which the pressure is read at up to 2m away from the mask at the flow generator.

One difference between the patient interface of the second sample embodiment and the patient interface of the first sample embodiment is that patient interface of the second sample embodiment may be, with minor modifications, mounted on any mask, whereas the patient interface of the first sample embodiment requires a customized mask.

It should be appreciated that the design considerations discussed above are not exhaustive. Other design considerations may also be accounted for by the sample embodiments described above. For example, the visual appearance of the mask and flow generator system, humidification of the pressurized flow, the safety of the oxygen delivery, sterilization of the system, fail safety procedures and precautions, and ergonomic issues may all be considered in the design of the system of the present invention.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes~morbid obesity, stroke, barriatric surgery, etc.) can derive benefit from the above teachings. Moreover, the above teachings have applicability with patients and non-patients alike in non-medical applications.

What is claimed is:

1. A system for delivering a pressurized flow of breathable gas to a patient, the system comprising:
    a patient interface configured to contact the patient's head, the patient interface comprising a frame and a cushion supported by the frame and configured to sealingly connect the patient interface to the patient's face and form a chamber between the frame and the patient's face, an inlet port in the frame is configured to receive the pressurized flow of breathable gas;
    a flow generator mounted on the patient interface, the flow generator being configured to generate the pressurized flow, capable of creating a pressure of about 2-40 cm $H_2O$ in the chamber;
    a pressure sensor assembly spanning from the flow generator to a wall of the patient interface, the pressure sensor assembly comprising a pressure sensor attached to the flow generator, a pressure port in the patient interface, and a tube connecting the pressure port to the pressure sensor; and
    a vibration dampening and/or noise absorbing material positioned between the pressure sensor and the flow generator,
    wherein the flow generator is connected to the patient interface by way of a support arm that is configured to minimize the transmission of vibrations between the patient interface and the flow generator,
    wherein the tube connecting the pressure port to the pressure sensor is positioned superior to the inlet port and inferior to the support arm, and
    wherein the support arm is a first support arm and the system further comprises a second support arm, the first and second support arms being positioned in a side-by-side arrangement and superior to the inlet port.

2. The system of claim 1, wherein the flow generator comprises an outlet port configured to discharge the pressurized flow to the inlet port of the patient interface and form a first gas flow path between the flow generator and the patient interface, and wherein the tube of the pressure sensor assembly forms a second gas flow path that is separate from the first gas flow path.

3. The system of claim 1, wherein the flow generator comprises a motor, an impeller powered by the motor, and a flow generator housing that encloses the motor and the impeller, wherein the pressure sensor is enclosed by a pressure sensor housing, and wherein the pressure sensor housing is located on an exterior surface of the flow generator housing.

4. The system of claim 1, further comprising a user interface configured to receive signals from the pressure sensor assembly and configured to control the flow generator based on the signals received from the pressure sensor assembly.

5. The system of claim 3, wherein the flow generator housing includes the vibration dampening and/or noise absorbing material.

6. The system of claim 5, wherein at least a portion of the flow generator housing is integrally formed with the frame of the patient interface.

7. The system of claim 5, wherein the vibration dampening and/or noise absorbing material is positioned between the flow generator housing and the motor and the impeller of the flow generator.

8. The system of claim 1, further comprising a user interface configured to receive signals from the pressure sensor assembly,
    wherein the flow generator comprises an outlet port configured to discharge the pressurized flow to the inlet port of the patient interface and form a first gas flow path between the flow generator and the patient interface,
    wherein the tube of the pressure sensor assembly forms a second gas flow path that is separate from the first gas flow path,
    wherein the flow generator comprises a motor, an impeller powered by the motor, and a flow generator housing that encloses the motor and the impeller,
    wherein the pressure sensor is enclosed by a pressure sensor housing,
    wherein the pressure sensor housing is located on an exterior surface of the flow generator housing, wherein the user interface is configured to control the flow generator based on the signals received from the pressure sensor assembly, wherein the flow generator housing includes the vibration dampening and/or noise absorbing material, wherein at least a portion of the flow generator housing is integrally formed with the frame of the patient interface, and wherein the vibration dampening and/or noise absorbing material is positioned between the flow generator housing and the motor and the impeller of the flow generator.

9. A system for delivering a pressurized flow of breathable gas to a patient, the system comprising:

a patient interface configured to contact the patient's head, the patient interface comprising a frame and a cushion supported by the frame and configured to sealingly connect the patient interface to the patient's face and form a chamber between the frame and the patient's face, an inlet port in the frame is configured to receive the pressurized flow of breathable gas;

a flow generator mounted on the patient interface, the flow generator being configured to generate the pressurized flow, capable of creating a pressure of about 2-40 cm $H_2O$ in the chamber, the patient interface and the flow generator together forming a pressurized airflow path;

a pressure sensor assembly configured to detect a gas pressure within the patient interface, the pressure sensor assembly comprising a pressure sensor located at the flow generator and a conduit that pneumatically connects an interior of the patient interface to the pressure sensor; and a vibration dampening and/or noise absorbing material positioned between the pressure sensor and the flow generator, wherein the flow generator is connected to the patient interface by way of a support arm that is configured to minimize the transmission of vibrations between the patient interface and the flow generator, wherein the pressure sensor is positioned superior to the inlet port and inferior to the support arm, and wherein the support arm is a first support arm and the system further comprises a second support arm, the first and second support arms being positioned in a side-by-side arrangement and superior to the inlet port.

10. The system of claim 9, wherein the flow generator comprises a motor, an impeller powered by the motor, and a flow generator housing that encloses the motor and the impeller, wherein the pressure sensor is enclosed by a pressure sensor housing, and wherein the pressure sensor housing is located on an exterior surface of the flow generator housing.

11. The system of claim 10, wherein a lower portion of the flow generator housing has a greater diameter than an upper portion of the flow generator housing.

12. The system of claim 9, further comprising a user interface configured to receive signals from the pressure sensor assembly and configured to control the flow generator based on the signals received from the pressure sensor assembly.

13. The system of claim 9, wherein the patient interface comprises one of a plurality of dampening devices.

14. A system for delivering a pressurized flow of breathable gas to a patient, the system comprising:

a patient interface configured to contact the patient's head, the patient interface comprising a frame and a cushion supported by the frame and configured to sealingly connect the patient interface to the patient's face and form a chamber between the frame and the patient's face, an inlet port in the frame is configured to receive the pressurized flow of breathable gas;

a flow generator mounted on the patient interface, the flow generator being configured to generate the pressurized flow, capable of creating a pressure of about 2-40 cm $H_2O$ in the chamber, the patient interface and the flow generator together forming a pressurized airflow path;

a pressure sensor assembly configured to determine a pressure of pressurized gas flowing through the patient interface, the pressure sensor assembly comprising a pressure sensor located at the flow generator, a pressure port in the patient interface, and a tube connecting the patient interface to the pressure sensor at the flow generator; and a vibration dampening and/or noise absorbing material positioned between the pressure sensor and the flow generator, wherein the flow generator is connected to the patient interface by way of a support arm that is configured to minimize the transmission of vibrations between the patient interface and the flow generator, wherein the pressure port and the tube connecting the pressure sensor to the pressure port are located superior to the inlet port and inferior to the support arm, and wherein the support arm is a first support arm and the system further comprises a second support arm, the first and second support arms being positioned in a side-by-side arrangement and superior to the inlet port.

15. The system of claim 14, wherein the flow generator comprises a motor, an impeller powered by the motor, and a flow generator housing that encloses the motor and the impeller, wherein the pressure sensor is enclosed by a pressure sensor housing, and wherein the pressure sensor housing is located on an exterior surface of the flow generator housing.

16. The system of claim 14, further comprising a user interface configured to receive signals from the pressure sensor assembly and configured to control the flow generator based on the signals received from the pressure sensor assembly.

* * * * *